United States Patent [19]

D'Souza et al.

[11] Patent Number: 5,403,824
[45] Date of Patent: Apr. 4, 1995

[54] METHODS FOR THE TREATMENT OF OSTEOPOROSIS

[75] Inventors: Sharyn M. D'Souza; Kenneth J. Ibbotson, both of Cincinnati, Ohio

[73] Assignee: The Procter & Gamble Company, Cincinnati, Ohio

[21] Appl. No.: 34,930

[22] Filed: Mar. 19, 1993

[51] Int. Cl.$^6$ .............................................. A61K 38/00
[52] U.S. Cl. ........................................ 514/12; 514/14; 514/15; 514/16; 514/17; 514/18; 514/19
[58] Field of Search ................................ 514/12, 14–19

[56] References Cited

U.S. PATENT DOCUMENTS

| | | | |
|---|---|---|---|
| 4,178,284 | 12/1979 | Sarantakis | 260/112.5 R |
| 4,213,968 | 7/1980 | Kastin et al. | 424/177 |
| 4,380,535 | 4/1983 | Sarantakis | 424/177 |
| 4,599,361 | 7/1986 | Dickens et al. | 514/575 |
| 4,617,149 | 10/1986 | DiMarchi et al. | 530/324 |
| 4,743,587 | 5/1988 | Dickens et al. | 514/575 |
| 4,822,609 | 4/1989 | Flora | 424/112 |

FOREIGN PATENT DOCUMENTS 2607701  6/1988  France .................. C07D 207/16

OTHER PUBLICATIONS

Pointillart et al, J. Anim. Sci. vol. 69 p. 1454 (1991).
Fournie-Zaluski et al, Biochem, Biophys Des. Comm. 94, 130–135 (1979).
K. L. King, J. Hua, J. S. Torday, J. M. Drazen, S. A. Graham, M. A. Shipp & M. E. Sunday, *J. Clin. Invest.*, vol. 9, pp. 1969–1973, "CD10/Neutral Endopeptidase 24.11 Regulates Fetal Lung Growth and Maturation in Utero by Potentiating Endogenous Bombesin-like Peptides", 1993.
S. Howell, A. M. Caswell, A. J. Kenny & A. J. Turner, *Biochem. J.*, vol. 290, pp. 159–164, "Membrane Peptidases on Human Osteoblast-like Cells in Culture: Hydrolysis of Calcitonin and Hormonal Regulation of Endopeptidase-24.11", 1993.
Y. Xiao-Li, T. Yu-Huan, & Z. Xiao-Ping & W. Shao, *Acta Pharmacologica Sinica*, vol. 13 pp. 156–158, "Central Analgesic Action of Calcitonin and its Relationship with Central Monoamine Transmitters", 1992.
M. Freirs-Garabel, M. T. Castano, A. Belmonte, J. Jorge, J. Couceiro & M. J. Nunez., *Neuroendocronology*, vol. 55, pp. 357–359, "Autoradiographic Evidence of Opioid Binding Sites in Rat Growth Plate Chondrocytes", 1992.
P. M. Villiger & Matrin Lotz, *The EMBO Journal*, vol. 11, No. 1, pp. 135–143, "Expression of Preproenkephalin in Human Articular Chondrocytes is Linked to Cell Proliferation", 1992.
R. D. Polakiewicz, O. Z. Behar, M. J. Comb, & H. Rosen, *Molecular Endocrinology*, vol. 6, No. 3, pp. 399–408, "Regulation of Proenkephalin Expression in Cultured Skin Mesenchymal Cells", 1992.
K. J. Ibbotson, S. M. D'Souza, M. Deschodt-Ianckman & T. E. Appelboom, *Journal of Bone and Mineral Research*, vol. 7, No. 3, pp. 273–279, "Inhibition of Bone Resorption In Vitro by Human Enkephalinase (EC 3.4.24.11), a Neutral Metalloendopeptidase", 1992.
D. T. Villareal, W. A. Murphy, S. L. Teitelbaum, M. Q. Arens & M. P. Whyte, *The American Journal of Medicine*, vol. 93, 371–381, "Painful Diffuse Osteosclerosis After Intravenous Drug Abuse", 1992.
H. Rosen, R. D. Polakiewicz, S. Benzakine, & Z. Bar-Shavit, *Proc. Natl. Acad. Sci. USA*, vol. 88, pp. 3705–3709, "Proenkephalin A in Bone-Derived Cells", 1991.

(List continued on next page.)

Primary Examiner—Jill Warden
Assistant Examiner—Sheela J. Huff
Attorney, Agent, or Firm—Carl J. Roof; Brahm J. Corstanje; David L. Suter

[57] ABSTRACT

Methods of treatment for osteoporosis in a human or other animal subject, comprising administering to said subject a safe and effective amount of an active selected from the group consisting of opioids, opioid-degrading enzyme inhibitors, enkephalin secretagogues, and mixtures thereof.

30 Claims, No Drawings

OTHER PUBLICATIONS

C. Gennari, D. Agnusdei & A. Camporeale, *Calcified Tissue International*, vol. 49, pp. S9–S13, "Use of Calcitonin in the Treatment of Bone Pain Associated with Osteoporosis", 1991.

N. Sales, I. Dutriez, B. Maziere, M. Ottaviani & B. P. Roques, *Regulatory Peptides*, vol. 33, pp. 209–222, "Neutral Endopeptidase 24.11 in Rat Peripheral Tissues: Comparative Localization by 'ex vivo' and 'in vitro' autoradiography", 1991.

J. Pfeilschifter, L. Bonewald & G. R. Mundy, *Handbook of Experimental Pharmacology*, pp. 371–400, "Role of Growth Factors in Cartilage and Bone Metabolism", 1991.

F. H. Hucklebrige, B. N. Hudspith, P. M. Lydyard & J. Brostoff, *Immunopharmacology*, vol. 19, pp. 87–91, "Stimulation of Human Peripheral Lymphocytes by Methionine Endephalin and δ-Selective Opioid Analogues", 1990.

R. D. Polakiewicz & H. Rosen, *Molecular and Cellular Biology*, vol. 10, No. 2, pp. 736–742, "Regulated Expression of Proenkephalin A During Ontogenic Development of Mesencyhmal Derivative Tissues":, 1990.

E. Keshet, R. D. Polakiewicz, A Itin, A. Ornoy & H. Rosen, *The EMBO Journal*, vol. 8, No. 10, pp. 2917–2923, "Proenkephalin A is Expressed in Mesodermal Lineages During Organogenesis" 1989.

I. S. Zagon & P. J. McLaughlin, *Brain Research*, vol. 412, pp. 68–72, "Endogenous Opioid Systems Regulate Cell Proliferation in the Developing Rat Brain" 1987.

L. Laurian, Z. Oberman, E. Graf, S. Gilad, E. Hoerer & R. Simantov, *Simantov, Horm. Metabol. Res.*, vol. 18, pp. 268–271, "Calcitonin Induced Increase in ACTH, β-Endorphin and Cortisol Secretion", 1986.

F. A. Tschopp, H. Henke, J. B. Petermann, P. H. Tobler, R. Janzer, T. Hökfelt, J. M. Lundberg, C. Cuello & J. A. Fischer, *Proc. Natl. Acad. Sci. USA*, vol. 82, pp. 248–252, "Calcitonin Gene-Related Peptide and its Binding Sites in the Human Central Nervous System and Pituitary", 1985.

A. Pecile, *Triangle*, vol. 22, No. 2/3, pp. 147–155, "Calcitonin and Pain Relief", 1983.

C. Gennari, *Triangle*, vol. 22, No. 2/3, pp. 157–163, "Clinical Aspects of Calcitonin in Pain", 1983.

J. A. Fischer P. H. Tobler, M. Kaufmann, W. Born, H. Henke, P. E. Cooper, S. M. Sagar & J. B. Martin, *Proc. Natl. Acad. Sci. USA*, vol. 78, No. 12, pp. 7801–7805, "Calcitonin: Regional Distribution of the Hormone and its Binding Sites in the Human Brain and Pituitary", 1981.

R. F. L. Bates, G. A. Buckley, R. M. Eglen & R. J. Strettle, *Proceedings of the B.P.S., 1st–3rd Apr., 1981*, "The Interaction of Naloxone and Calcitonin in the Production of Analgesia in the Mouse", 1981.

P. Braga, S. Ferri, A. Santagostino, V. R. Olgiati & A. Pecile, *Life Sciences*, vol. 22, pp. 971–978, "Lack of Opiate Receptor Involvement in Centrally Induced Calcitonin Analgesia", 1978.

A. Dupont, L. Cusan, M. Garon, F. Labrie & C. H. Li, *Proc. Natl. Acad. Sci. USA*, vol. 74, No. 1, pp. 358–359, "β-Endorphin: Stimulation of Growth Hormone Release in vivo", 1977.

C. Rivier, W. Vale, N. Ling, M. Brown & R. Guillemin, *Endocrinology* vol. 100, pp. 238–241, "Stimulation in vivo of the Secretion of Prolactin and Growth Hormone by β-Endorphin", 1977.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( D ) TOPOLOGY: linear ( x i ) SEQUENCE DESCRIPTION: SEQ ID NO:1:

```
Tyr  Gly  Gly  Phe  Met  Thr  Ser  Glu  Lys  Ser  Gln  Thr  Pro  Leu  Val  Thr
 1                  5                       10                           15
Leu  Phe  Lys  Asn  Ala  Ile  Ile  Lys  Asn  Ala  His  Lys  Lys  Gly  Gln
                20                      25                       30
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:2:

Tyr  Gly  Gly  Phe  Met
1                     5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:3:

Tyr  Gly  Gly  Phe  Leu
1                     5

METHODS FOR THE TREATMENT OF OSTEOPOROSIS

BACKGROUND OF THE INVENTION

This invention relates to methods of building bone in humans and other animals, i.e., for the treatment of osteoporosis and related disorders. In particular, this invention relates to such methods of treatment by administration of opioids, opioid-degrading enzyme inhibitors, enkephalin secretagogues, or mixtures thereof.

The most common metabolic bone disorder is osteoporosis. Osteoporosis can be generally defined as the reduction in the quantity of bone, or the atrophy of skeletal tissue. In general, there are two types of osteoporosis: primary and secondary. "Secondary osteoporosis" is the result of an identifiable disease process or agent. However, approximately 90% of all osteoporosis cases is "primary osteoporosis". Such primary osteoporosis includes postmenopausal osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. Th is remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there is an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Many compositions and methods are described in the medical literature for the "treatment" of osteoporosis. Many of these compositions and methods attempt to either slow the loss of bone or to produce a net gain in bone mass. See, for example, R. C. Haynes, Jr. et al., "Agents Affecting Calcification", *The Pharmacological Basis of Therapeutics*, 7th Edition (A. G. Gilman, L. S. Goodman et al., Editors, 1985); G. D. Whedon et al., "An Analysis of Current Concepts and Research Interest in Osteoporosis", *Current Advances in Skeletogenesis* (A. Ornoy et al., Editors, 1985); and W. A. Peck, et al., *Physician's Resource Manual on Osteoporosis* (1987), published by the National Osteoporosis Foundation.

Among the treatments for osteoporosis suggested in the literature is the administration of bisphosphonates or other bone-active phosphonates. See, for example, Storm et al., "Effect of Intermittent Cyclical Etidronate Therapy on Bone Mineralization and Fracture Rate in Women with Post-Menopausal Osteoporosis", 322 *New England Journal of Medicine* 1265 (1990); and Watts et al., "Intermittent Cyclical Etidronate Treatment of Post-Menopausal Osteoporosis", 323 *New England Journal of Medicine* 73 (1990). Such treatments using a variety of bisphosphonates are described in, for example, U.S. Pat. No. 4,761,406, Flora et al., issued Aug. 2, 1988; U.S. Pat. No. 4,812,304, Anderson et al., issued Mar. 14, 1989; U.S. Pat. No. 4,812,311, Uchtman, issued Mar. 14, 1989; and U.S. Pat. No. 4,822,609, Flora, issued Apr. 18, 1989. The use of such phosphonates for the treatment of osteoporosis, and other disorders involving abnormal calcium and phosphate metabolism, is also described in U.S. Pat. No. 3,683,080, Francis, issued Aug. 8, 1972; U.S. Pat. No. 4,330,537, Francis, issued Oct. 28, 1980; U.S. Pat. No. 4,267,108, Blum et al., issued May 12, 1981; European Patent Publication 298,553, Ebetino, published Jan. 11, 1989; and Francis et al., "Chemical, Biochemical, and Medicinal Properties of the Diphosphonates", *The Role of Phosphonates in Living Systems* 55 (1983).

Administration of estrogen is also used as a means to prevent osteoporosis in postmenopausal women. This therapy typically involves daily administration of from about 0.625 milligrams to about 1.25 milligrams of conjugated estrogens, or equivalent amounts of other estrogen hormones. Estrogen may also be used to treat osteoporosis, although this has not been fully established. See, for example, Barzel, "Estrogens in the Prevention and Treatment of Post-Menopausal Osteoporosis: Is it Effective?" *Hospital Practice* 95 (1990); Ettinger, et al., "Post-Menopausal Bone Loss is Prevented by Treatment with Low-Dosage Estrogen with Calcium", 106 *Annals in Internal Medicine* 40 (1987); Lindsay, et al., "The Minimum Effective Dose of Estrogen for Prevention of Post-Menopausal Bone Loss", 63 *Obstetrics and Gynecology* 759 (1984); and "Estrogen", *Drug Information* 1765 (1990).

While estrogen may be useful in preventing (and, potentially treating) osteoporosis and other bone metabolism disorders, the use of estrogen has been associated with certain side effects, such as uterine bleeding. See, Rudy, "Hormone Replacement Therapy—How to Select the Best Preparation and Regimen," 88 *Postgraduate Medicine* 157 (1990). In addition, long-term estrogen therapy has been linked to an increased risk of endometrial carcinoma and inflammatory gallbladder disease. See Id.

In spite of the many compositions and methods described in the art, there is a continuing need for new safe and effective methods of treating bone metabolism disorders. As indicated, there are potential side effects associated with estrogen therapy. Similarly, phosphonate therapy (particularly bisphosphonate therapy) may result in certain side effects. For example, bisphosphonates are known to prevent bone loss by inhibiting bone resorption. Because bone resorption is coupled with bone formation, bisphosphonates generally inhibit the rate of bone formation.

It is therefore an object of the present invention to provide methods useful in treating osteoporosis and related disorders. Applicants have found that, surprisingly, osteoporosis may be treated by administering opioids, opioid-degrading enzyme inhibitors, enkephalin secretagogues, or mixtures thereof.

SUMMARY OF THE INVENTION

The present invention provides methods of treatment of osteoporosis in a human or other animal subject, comprising administering to said subject a safe and effective amount of a compound selected from opioids, opioid-degrading enzyme inhibitors, enkephalin secretagogues, and mixtures thereof.

DESCRIPTION OF THE INVENTION

The methods of the present invention comprise the administration of opioids, opioid-degrading enzyme inhibitors, enkephalin secretagogues, and mixtures thereof, to a human or other animal subject. These methods of administration preferably provide increased levels of opioids in vivo. That is, in vivo levels of opioids are increased exogenously and/or endogenously as a result of methods of the present invention. Opioid levels may be increased endogenously by stimulation of opioid release in vivo, by inhibition of in vivo opioid degradation, or via both mechanisms.

Specific compounds and compositions to be used in the methods of the present invention must be pharmaceutically-acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the specific active(s) being administered, the duration of the treatment, the nature of concurrent therapy (if any), and the specific formulations employed.

Definitions

The following is a list of terms used herein.

"Class of actives" refers to each of the three classes of compounds described herein, namely: "opioids", "opioid-degrading enzyme inhibitors", and "enkephalin secretagogues".

"Active" is a particular compound within one of these classes of actives.

"Lower alkyl" is an unsubstituted or substituted saturated hydrocarbon chain radical having from 1 to 6 carbon atoms, preferably from 1 to 4 carbon atoms. Preferred alkyl groups include (for example) methyl, ethyl, propyl, isopropyl, and butyl.

"Heteroatom" is a nitrogen, sulfur, or oxygen atom.

"Carbocyclic ring" is an unsubstituted or substituted, saturated, unsaturated or aromatic, hydrocarbon ring radical.

"Heterocyclic ring" is an unsubstituted or substituted, saturated, unsaturated or aromatic ring radical comprised of carbon atoms and one or more heteroatoms in the ring.

"Aryl" is an aromatic carbocyclic ring radical. Preferred aryl groups include substituted or unsubstituted phenyl groups.

"Arylalkyl" is an alkyl radical substituted with an aryl group. Preferred arylalkyl groups include phenylmethyl ( i.e., benzyl) and phenyl ethyl.

"Benzene sulfonic acid" is the radical

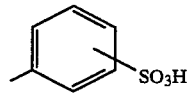

"Heteroaryl" is an aromatic heterocyclic ring radical. A preferred heteroaryl is pyridyl.

"Pharmaceutically-acceptable salts" is a cationic salt formed at any acidic (e.g. carboxyl) group, or an anionic salt formed at any basic group (e.g. amino) group. Many such salts are known in the art, as described in World Patent Publication 87/05297, Johnston et al., published Sep. 11, 1987, which is incorporated by reference herein. Preferred cationic salts include the alkali metal salts (such as sodium and potassium), and alkaline earth metal salts (such as magnesium and calcium). Preferred anionic salts include the halides (such as chloride salts).

As defined above and as used herein, substituent groups may themselves be substituted. Such substitution may be with one or more substituents.

"Amino acid residue" refers to an amino acid that is linked to one or more amino acids to form a peptide. An amino acid residue may be bonded to another amino acid at its α-carboxy position, its α-amino position, or both its α-carboxy and its α-amino positions.

"Peptide linkage" is formed by the joining of the α-carboxyl group of one amino acid residue to the α-amino group of another amino acid residue (with the loss of a water molecule). When two amino acids are joined by a peptide linkage, the resulting "peptide linking group" is —C(=O)—NH—.

"Isosteric linkage" is formed by the joining of two amino acid residues wherein either or both the α-carbonyl and α-amino groups are replaced by a non-hydrolyzable group. When two amino acids are joined by an isosteric linkage, the resulting "isosteric linking groups" include, for example, ketomethylene [—C(=O)—CH$_2$—], hydroxyethylene [—CH(OH)—CH$_2$—], methyleneoxy [—CH$_2$—O—], methylenethio [—CH$_2$—S—], and trans-alkene [trans—CH=CH—]. Examples of various isosteric linkages, and methods for preparing peptides having such linkages, are described in U.S. Pat. No. 4,198,398, to Hudson et al., issued Apr. 15, 1980, which is incorporated herein by reference.

"D-Ser(O-t-butylether)" is a substituted serine amino acid residue having the structure:

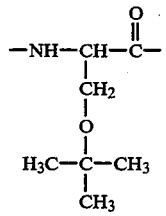

where the substituted serine amino acid is of the D-configuration and is either a terminal or non-terminal amino acid residue of a peptide.

"D-Cys(S-t-butylthioether)" is a substituted cysteine amino acid residue having the structure:

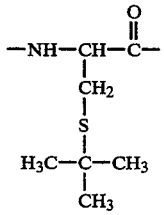

where the substituted cysteine amino acid is of the D-configuration and is either a terminal or non-terminal amino acid residue of a peptide.

"D-Met(sulfoxide)" is a substituted methionine amino acid residue having the structure:

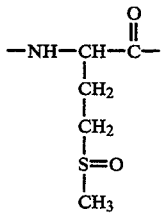

where the substituted methionine amino acid is of the D-configuration and is either a terminal or non-terminal amino acid residue of a peptide.

"Phe(ol)" is a phenylalanine amino acid residue having the structure:

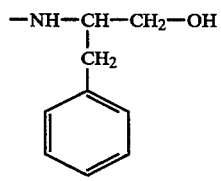

where the phenylalanine amino acid is a carboxy-terminal amino acid residue of a peptide and the carboxyl group of the terminal phenylalanine is replaced by a methylene alcohol group.

"Met(sulfoxide)(ol)" is a substituted methionine amino acid residue having the structure:

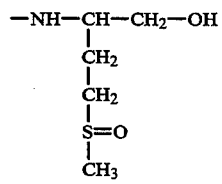

where the substituted methionine amino acid is a carboxy-terminal amino acid residue of a peptide and the carboxyl group of the terminal, substituted methionine is replaced by a methylene alcohol group.

"Thr(O-t-butylether)" is a substituted threonine amino acid residue having the structure:

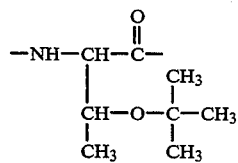

where the substituted threonine amino acid is either a terminal or non-terminal amino acid residue of a peptide.

"Gly(ol)" is

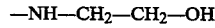

$-NH-CH_2-CH_2-OH$ where the glycine amino acid is a carboxy-terminal amino acid residue of a peptide and the carboxyl group of the terminal glycine is replaced by a methylene alcohol group.

"D-Pen" is D-penicillamine.

"Nle" is norleucine.

"Ile" is isoleucine.

"Statistically significant", "significant", etc. are used interchangeably. Statistical significance can be determined by any of several statistical techniques. An accepted definition of statistically significant is $p \leq 0.05$, using analysis of variance with Neuman-Keuls test and critical ranges.

The three letter abbreviations used herein to represent amino acids are consistant with the three letter abbreviations provided in 37 C.F.R. 1.822(b)(2). Where no designation is given as to the D- or L- stereochemical configuration, both stereoisomers forms are included.

Other terms are defined at their location of use in the specification.

Active Materials

Opioids

Among the methods of this invention is the administration of opioids. The literature indicates that at least (3) major sub-classes of opioid receptors (delta, mu, and kappa) have been identified. See, for example, A. Goldstein et al., "Multiple Opioid Receptors: Ligand Selectivity Profiles and Binding Site Signatures", 36 *Cellular Pharmacology* 265–272 (1989).

As referred to herein, an "opioid" is any compound that has affinity for opioid receptors. Preferred "opioids" are those compounds that have affinity for mu opioid receptors and/or those compounds that have affinity for delta opioid receptors.

Opioids useful in the methods of the present invention preferably act on the peripheral terminals of primary afferent nerves. That is, preferred opioids are those opioids that do not exhibit activity via the central nervous system (CNS).

Particularly preferred opioids useful in the methods of the present invention are those compounds that demonstrate significant in vitro affinity for mu opioid receptors and/or those compounds that demonstrate significant in vitro affinity for delta opioid receptors. Several in vitro models for assessing affinity of opioids for a particular sub-class of opioid receptors are described in the literature. See U.S. Pat. No. 4,910,152, to Meyers et al., issued Mar. 20, 1990, which is incorporated herein by reference. In general, these models determine whether a test compound has opioid receptor affinity by measuring that compound's ability to inhibit binding to opioid receptors by a radiolabeled ligand known to have opioid receptor affinity.

Affinity for mu opioid receptors can be measured by any of several art-recognized in vitro models. One such model is described by A. Goldstein et al., "Multiple Opioid Receptors: Ligand Selectivity Profiles and Binding Site Signatures", 36 *Cellular Pharmacology* 265–272 (1989), which is incorporated herein by reference. According to this model, a test compound is screened for its ability to inhibit binding of a mu-selective radiolabeled ligand ("mu-selective radiolabeled ligand" refers to a radiolabeled compound that is known to have selective affinity for mu opioid receptors) to mu opioid receptor binding sites. More specifically, this in vitro model compares test samples (comprising a mu-selective radiolabeled ligand ("hot ligand"); the non-radiolabeled equivalent to the "hot ligand" ("cold ligand"); test compound at varying concentrations in each test sample; and mu opiate receptor material) and a control sample (comprising hot ligand; cold ligand; and mu opiate receptor material).

Following the protocol set forth by Goldstein et al., the samples are assayed for relative radioactivity. (If the test compound has affinity for mu receptors, it will occupy a significant number of the mu receptor binding sites. As a result, the test samples will demonstrate significantly less radioactivity than the control samples containing only the radiolabeled ligand.) From the assay, the $IC_{50}$ concentration (i.e., the concentration required to decrease the level of binding of "hot ligand" to mu opioid receptors by one-half ($\frac{1}{2}$)) can be determined for the test compound and the "cold ligand". As referred to herein, a test compound demonstrates "significant in vitro mu opioid receptor affinity" if that compound has an $IC_{50}$ concentration that is $\leq 1,000$ times the $IC_{50}$ concentration of the "cold ligand". Particularly preferred opioids are those compounds that demonstrate signficant in vitro mu opioid receptor affinity, according to the method described by Goldstein et al., or a similar in vitro model.

In assessing a compound's in vitro affinity for mu opioid receptors according the method described by Goldstein et al., the mu-selective radiolabeled ligand (i.e., "hot ligand") is preferrably [³H]Tyr-D-Ala-Gly-N-methyl-Phe-Gly(ol) ("[³]DAGO" or "hot DAGO"). The preferred "cold ligand" is therefore Tyr-D-Ala-Gly-N-methyl-Phe-Gly(ol) ("DAGO" or "cold DAGO"). A preferred source of mu opioid receptors is guinea pig brain.

For purposes of hypothetical illustration only, if "hot DAGO" were used as the radiolabeled ligand and "cold DAGO" as the non-radiolabeled ligand, according to the above-described method, and the $IC_{50}$ concentration for "cold DAGO" was determined to be $1.00 \times 10^{-5}$M, any test compound having an $IC_{50}$ concentration of $\leq 1.00 \times 10^{-2}$M would have "significant in vitro mu opioid receptor affinity", according to the in vitro model described by Goldstein.

Numerous compounds are known to have mu opioid receptor affinity. Such compounds useful in the methods of this invention include H-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-His-Lys-Lys-Gly-Cln-OH; (SEQ ID NO: 1) Tyr-D-Ala-Gly-N-methyl-Phe- Gly(ol); H-Tyr-D-Ala-Gly-Phe-D-Leu-OH; morphine; and H-Tyr-D-Arg-Phe-Lys-NH₂.

Affinity for delta opioid receptors can be measured by any of several art-recognized in vitro models. One such model is described by Goldstein et al., and is discussed above. According to this model, a test compound is screened for its ability to inhibit binding of a delta-selective radiolabeled ligand ("delta-selective radiolabeled ligand" refers to a radiolabeled compound that is known to have selective affinity to delta opioid receptors) to delta opioid receptor binding sites. More specifically, this in vitro model compares test samples (comprising a delta-selective radiolabeled ligand ("hot ligand"); the non-radiolabeled equivalent to the "hot ligand" ("cold ligand"); test compound at varying concentrations in each test sample; and delta opiate receptor material) and a control sample (comprising hot ligand; cold ligand; and delta opiate receptor material).

Following the protocol set forth by Goldstein et al., the samples are assayed for relative radioactivity. (If the test compound has affinity for delta receptors, it will occupy a significant number of the delta receptor binding sites. As a result, the test samples will demonstrate significantly less radioactivity than the control samples containing only the radiolabeled ligand.) From the assay, the $IC_{50}$ concentration (i.e., the concentration required to decrease the level of binding of "hot ligand" to delta opioid receptors by one-half ($\frac{1}{2}$)) can be determined for the test compound and the "cold ligand". As referred to herein, a test compound demonstrates "significant in vitro delta opioid receptor affinity" if that compound has an $IC_{50}$ concentration that is $\leq 1,000$ times the $IC_{50}$ concentration for "cold ligand". Particularly preferred opioids are those compounds that demonstrate signficant in vitro delta opioid receptor affinity, according to the method described by Goldstein et al., or a similar in vitro model.

In assessing a compound's in vitro affinity for delta opioid receptors according to the method described by Goldstein et al., the delta-selective radiolabeled ligand ("hot ligand") is preferrably [³H]Tyr-D-Pen-Gly-Phe-D-Pen-OH ("[³H]-DPDPE"). The preferred "cold ligand" is therefore H-Tyr-D-Pen-Gly-Phe-D-Pen-OH ("cold DPDPE" or "DPDPE"). A preferred source of delta opioid receptors is guinea pig brain.

For purposes of hypothetical illustration only, if "hot DPDPE" were used as the radiolabeled ligand and "cold DPDPE" as the non-radiolabeled ligand, according to the above-described method, and the $IC_{50}$ concentration for "cold DPDPE" was determined to be $1.0 \times 10^{-5}$M, any test compound having an $IC_{50}$ concentration of $\leq 1.0 \times 10^{-2}$M would have "significant in vitro delta opioid receptor affinity", according to the in vitro model described by Goldstein.

Numerous compounds are known in the art to have delta opioid receptor affinity. Such compounds useful in the methods of this invention include, for example, diprenorphine, H-Tyr-D-Pen-Gly-Phe-D-Pen-OH; H-Tyr-D-Thr-Gly-Phe-Leu-Thr-OH; H-Tyr-D-Ser-Gly-Phe-Leu-Thr-OH; H-Tyr-D-Ala-Gly-Phe-Leu-OH; H-Tyr-D-Ala-Gly-Phe-Leu-Thr-OH; H-Tyr-D-Ala-Gly-Phe-D-Leu-OH; H-Tyr-D-Cys(S-t-butylether)-Gly-Phe-Leu-Thr(O-t-butylether)-OH; H-Tyr-D-Ser-(O-t-butylether)-Gly-Phe-Leu-Thr-OH; and H-Tyr-D-Ser(O-t-butylether)-Gly-Phe-Leu-Thr(O-t-butylether)-OH.

As indicated, particularly preferred opioids useful in the methods of the present invention are those compounds that demonstrate significant in vitro mu opioid receptor affinity and/or demonstrate significant in vitro delta opioid receptor affinity, according to the method described by Goldstein et al., or a similar in vitro assay. If a compound that demonstrates significant in vitro mu opioid receptor affinity and/or demonstrates significant in vitro delta opioid receptor affinity according to this method also exhibits in vitro affinity for opioid receptors other than the mu or delta receptors (e.g. kappa receptors), that compound is still a particularly preferred opioid useful in the methods of the present invention.

Preferred compounds useful in methods of the present invention include those compounds that significantly stimulate osteoblast-like cell proliferation. Stimulation of osteoblast-like cell proliferation can be measured according to several art-recognized in vitro models. One such model is described in European Patent Publication No. 384,731, by Rodan et al, published Aug. 29, 1990, which is incorporated herein by reference. (Applicants have modified this method by reducing regent volumes to one-quarter those described and by utilizing Dulbecco's Modified eagle's Medium (DMEM).) In this model, proliferation (division) of, for example, rat osteoblast-like cells (rat osteosarcoma (ROS) cells, rat calvaria cells, etc.) is observed by measuring the amount of radiolabeled thymidine ([$^3$H]thymidine) incorporated by these cells. ([$^3$H]thymidine is "incorporated" by cellular DNA being synthesized as a result of cell proliferation.) The greater the level of [$^3$H]thymidine measured, the greater the amount of proliferation of the osteoblast cells.

More specifically, a test sample (comprised of a test compound and osteoblast-like cells) and a control sample (comprised of only osteoblast-like cells) are pulsed with [$^3$H]thymidine. The amount of [$^3$H]thymidine incorporated by the cells is measured using a direct beta counter. If significantly more [$^3$H]thymidine is "incorporated" by the cells of the test sample than the cells of the control sample, the test compound is said to "significantly stimulate osteoblast-like cell proliferation".

Preferred opioids are those opioids that are shown to significantly stimulate osteoblast-like cell proliferation in vitro.

A particularly preferred opioid useful in the methods of the present invention is H-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-His-Lys-Lys-Gly-Gln-OH(SEQ ID NO: 1).

Particularly preferred opioids useful in the methods of the present invention are enkephalins. Numerous enkephalins, and methods for their preparation, are described in the art and are useful in the methods of the present invention. Such enkephalins are described in the following references, all of which are incorporated by reference: U.S. Pat. No. 4,468,383, to Rodbard et al., issued Aug. 28, 1984; U.S. Pat. No. 4,371,463, to Pert et al., issued Feb. 1, 1983; U.S. Pat. No. 4,261,883, to Smolarsky, issued Apr. 14, 1981; U.S. Pat. No. 4,254,106, to Wilkinson, issued Mar. 3, 1981; U.S. Pat. No. 4,213,968, to Kastin et al., issued Jul. 22, 1980; U.S. Pat. No. 4,198,398, to Hudson et al., issued Apr. 15, 1980; U.S. Pat. No. 4,127,534, to Coy et al., issued Nov. 28, 1978; U.S. Pat. No. 4,092,304, to Jone, Jr. et al., issued May 30, 1978; U.S. Pat. No. 4,028,319, to Jones, Jr. et al., issued Jun. 7, 1977; J. Chang et al., "Opiate Receptor Affinities and Behavioral Effects of Enkephalin: Structure Activity Relationship of Ten Synthetic Peptide Analogues," 18 *Life Sci.* 1473-1482 (1976); G. A. Gacel et al., "Synthesis, Biochemical and Pharmacological Properties of BUBUC, a Highly Selective and Systematically Active Agonist for In Vivo Studies of Delta-Opioid Receptors", 11 *Peptides* 983-988 (1990); and B. P. Roques, "Peptidomimetics as Receptor Agonists or Peptidase Inhibitors: A Structural Approach in the Field of Enkephalins, ANP and CCK", 32 *Biopolymers* 407-410 (1992).

Preferred enkephalins useful in the methods of the present invention are polypeptides having from 2 to 15 amino acids (preferably 2 to 8 amino acids, more preferably 2 to 6 amino acids), where said polypeptide is comprised in part by a polypeptide of the formula:

R-A-B-C-D-E-F-G-H-R$^1$ wherein
(1) R is hydrogen or lower alkyl;
(2) A is Tyr, 2,6 dimethyl-Tyr, or 2,6 dihalo-Tyr, where halo is independently selected from fluoro, chloro, bromo, or iodo;
(3) B is an L-amino acid residue, a D-amino acid residue, D-Ser(O-t-butylether), D-Cys(S-t-butylthioether), or D-Met(sulfoxide) (preferably a D-amino acid residue, Gly, D-Ser(O-t-butylether), D-Cys(S-t-butylthioether), or D-Met(sulfoxide); more preferably Gly, D-Ala, D-Arg, D-Met, D-Ser, D-Pen, D-Ser(O-t-butylether), D-Cys(S-t-butylthioether) or D-Met(sulfoxide));
(4) C is Gly, Phe, or nil;
(5) D is D' where D' is Phe, N-R$^2$-Phe, p-nitro-Phe, p-halo-Phe, Gly, or nil, where R$^2$ is lower alkyl and halo is fluoro, chloro, bromo, or iodo; or when E, F, G, H, and R$^1$ are nil, D is D' or Phe(ol) (preferably D is Phe, N-methyl-Phe, nil, or Phe(ol); most preferably D is Phe);
(6) E is E' where E' is an L-amino acid residue, a D-amino acid residue, D-Pen, or nil; or when F, G, H, and R$^1$ are nil, E is E', Met(sulfoxide)(ol), or Gly(ol) (E is preferably Leu, Met, Pro, Tyr, Nle, D-Pen, Gly(ol), Met(sulfoxide)(ol), or nil);
(7) F is F' where F' is nil, Thr, or Thr(O-t-butylether); or where both G and H are other than nil, F is F', Arg, or Lys (F is preferably Thr, Thr(O-t-butylether), or nil);
(8) G is nil; or where both F and H are other than nil, G is Arg, N-methyl-Arg, Lys or nil (G is preferably nil);
(9) H is nil; or where both F and G are other than nil, H is D-Leu, Arg, Lys, or nil (H is preferably nil); and
(10) R$^1$ is hydroxy, amino, -NHR$^3$, -N(R$^3$)(R$^4$), -O-R$^3$, 2-acetylhydrazine, 2-propanoylhydrazine, N-aryl-alkylamine, chloromethyl, or nil; wherein R$^3$ and R$^4$ are independently selected from methyl, ethyl, phenyl ethyl, or phenyl propyl;
and wherein each peptide bond may be replaced by an isosteric linkage groups.

Particularly preferred enkephalins useful in the methods of this invention include: H-Tyr-Gly-Gly-Phe-Met-OH (SEQ ID NO: 2); H-Tyr-Gly-Gly-Phe-Leu-OH (SEQ ID NO: 3); H-Tyr-D-Cys(S-t-butylether)-Gly-Phe-Leu-Thr(O-t-butylether)-OH; H-Tyr-D-Ser(O-t-butylether)-Gly-Phe-Leu-Thr-OH; H-Tyr-D-Ser (O-t-butylether)-Gly-Phe-Leu-Thr(O-t-butylether)-OH; H-Tyr-D-Ala-Gly-N-methyl-Phe-Met(sulfoxide)(ol); H-Tyr-D-Ser-Gly-Phe-Leu-Thr-OH; H-Tyr-D-Ala-Gly-Phe-D-Leu-OH; H-Tyr-D-Ala-Gly-Phe-Leu-NH$_2$; H-

Tyr-D-Ala-Gly-Phe-Met-NH$_2$; H-Tyr-D-Ala-Phe-Met-NH$_2$; H-Tyr-D-Met(sulfoxide)-Gly-Phe(ol); H-Tyr-D-Met-Gly-Phe-Pro-NH$_2$; H-2,6-dimethyl-Try-D-Ala-N-phenyl propyl amine; and H-Tyr-D-Pen-Gly-Phe-D-Pen; H-Tyr-D-Ala-Gly-N-methyl-Phe-Gly(ol); wherein each peptide bond may be replaced by an isosteric linkage group.

Opioid-Degrading Enzyme Inhibitors

It is known that peptidic opioids are degraded (cleaved) in vivo by certain enzymes. This susceptibility to in vivo degradation limits the suitability of peptidic opioids as pharmacological agents. It is also known that a class of compounds inhibit enzymatic cleavage of peptidic opioids. See H. Suh, et al., "Intrathecal Administration of Thiorphan and Bestatin Enhances the Antinociception and Release of Met-enkephalin Induced by Beta-Endorphin Intraventricularly in Anesthetized Rats", 16 *Neuropeptides* 91–96 (1990) and H. Suh, et al., "Intrathecal Administration of Theorphan, Bestatin, Desipramine and Fluoxetine Differentially Potentiate the Antinociceptive Effect Induced by Beta-Endorphin and Morphine, Administered Intracerebroventricularly", 29 *Neuropharm* 207–214 (1990).

Among the methods of this invention is the administration of "opioid-degrading enzyme inhibitors". As referred to herein, the term "opioid-degrading enzyme inhibitor" includes any compound that inhibits enzyme degradation of endogenous or exogenous peptidic opioids.

As indicated above, preferred opioids useful in the methods of the present invention are enkephalins. It is well known that enkephalins are degraded (cleaved) in vivo by certain enzymes. As with peptidic opioids generally, susceptibility to in vivo degradation limits the enkephalins' suitability as pharmacological agents. It is also well known that a class of compounds, generally referred to as enkephalin-degrading enzyme inhibitors, inhibit enzymatic cleavage of enkephalins. See for example U.S. Pat. No. 4,380,535, to Sarantakis, et al., issued Apr. 19, 1983, which is incorporated herein by reference.

Preferred opioid-degrading enzyme inhibitors are enkephalin-degrading enzyme inhibitors. As referred to herein, the term "enkephalin-degrading enzyme inhibitor" includes any compound that inhibits enzyme degradation of endogenous or exogenous enkephalin.

Preferred enkephalin-degrading enzyme inhibitors are those compounds that demonstrate significant in vitro inhibition of peptide degradation by an enkephalin-degrading enzyme. In vitro inhibition of enzymatic enkephalin degradation can be screened using any of several art-recognized in vitro models. In these models, a peptide ("substrate") is exposed to an enzyme known to degrade enkephalins. The substrate may either be an enkephalin or another peptidic substrate known to be susceptible to cleavage by a particular enkephalin-degrading enzyme. Degradation of the peptide results in liberation of specific metabolites. The amount of metabolite liberated (or peptide maintained) can be monitored to determine the degree of degradation of the substrate by the enzyme. That is, putative enzyme inhibitors can be tested to determine their propensity to reduce the amount of metabolite liberated by degradation of a particular substrate by a particular enzyme.

These in vitro models generally consist of a test sample (containing a putative enzyme inhibitor and a peptidic substrate) and a control sample (containing the substrate with no putative inhibitor). Each sample is exposed to a particular peptidase, and the samples are then compared to determine whether significantly more metabolite (or less substrate) is present in the control sample than in the test sample. If there is significantly more metabolite (or less substrate) in the control sample than the test sample, the test compound is an inhibitor of the enzyme(s) present.

One such model is described in U.S. Pat. No. 4,380,534, to Sarantakis et al. In this model, inhibitory potency of a test compound is evaluated by measuring the ability of the compound to inhibit enzymatic enkephalin degradation. More specifically, this model compares two study samples: a control sample (comprising the substrate [$^3$H]Tyr-Gly-Gly-Phe-Leu ("[$^3$H]Leu-enkephalin")) and a test sample (comprising [$^3$H]Leu-enkephalin and a putative enkephalin-degrading enzyme enzyme inhibitor). Upon equilibrium of these samples, a quantified amount of enzyme is added to each sample. After a specified reaction period, the reaction is terminated. The samples are measured for enkephalin degradation metabolites, the presence of which indicate that the particular enkephalin has been degraded by the enzyme. If the test sample contains significantly less degradation component(s) than does the control sample, the test compound demonstrates significant in vitro inhibition of peptide degradation by an enkephalin-degrading enzyme. As such, the test compound is a preferred enkephalin-degrading enzyme inhibitor.

A similar method for determining inhibitory potency is described in U.S. Pat. No. 4,423,242, to Wilkinson et al., issued Dec. 27, 1983, which is incorporated herein by reference. While the method is otherwise similar to that described in Sarantakis, the U.S. Pat. No. 4,423,242 describes the use of purified "enkephalinase" as the peptidic enzyme, not a mixture of enzymes. Thus, use of the method described by Wilkinson assesses a test compound's ability to inhibit degradation of enkephalin by the specific enzyme "enkephalinase".

As indicated, potency of putative enkephalin-degrading enzyme inhibitors may also be determined by in vitro models that utilize a substrate other than enkephalin. Various peptidic substrates are known to be cleaved by specific enkephalin-degrading enzymes. As such, inhibitory potency can be determined by the ability of a test compound to inhibit degradation of a substrate by a specific enzyme.

One such model is described by Spillantini et al., 12 *Eur. J. Pharmacol* 142–150 (1986), which has been modified by Applicants. (Applicants' modification consists of using osteoblast-like cells, rather than human serum, as the source of enkephalin-degrading enzymes.) This model measures inhibition of the enkephalin-degrading enzyme "enkephalinase". According to Applicants' modified method, the source of the enkephalin-degrading enzymes i s rat osteoblast-like cells or mouse osteoblast-like cells (MC3T3-E1 cells). The substrate used is N-succinyl-alanyl-alanyl-phenylalanyl-7-amido-4-methyl coumarin (hereafter N-suc-Ala-Ala-Phe-AMC), which is known to be cleaved at the Ala-Phe peptide bond by enkephalinase. Thus, cleavage by enkephalinase yields the metabolites N-suc-Ala-Ala and Phe-AMC. Aminopeptidase, which is known to specifically cleave only Phe-AMC (at the Phe-AM(peptide bond), is then added to the sample. Cleavage by aminopeptidase yields the metabolites AMC (fluorescent) and Phe. Fluorescence is then measured and is directly proportional to the amount of substrate degraded by enkephalinase.

Specifically, a test sample (containing enzyme and a putative enkephalinase inhibitor) and a control sample (containing only enzyme) are equilibrated. A quantified amount of substrate is then added to both samples. After incubation, aminopeptidase is added to each sample, followed by further incubation. Fluorescence of the samples is then measured, greater fluorescence corresponding to greater degradation of the substrate by enkephalinase. If significantly less fluorescence is seen in the test sample than the control sample, the test compound has demonstrated significant in vitro inhibition of peptide degradation by an enkephalin-degrading enzyme. Thus, the test compound is a preferred enkephalin-degrading enzyme inhibitor.

Another model that assesses the ability of a compound to inhibit degradation by enkephalin-degrading enzyme (in this model, the enzyme is aminopeptidase, a known enkephalin-degrading enzyme) is described by D. Mantle, et al., "Purification and Characterization of the Major Aminopeptidase From Human Skeletal Muscle", 211 *Biochem. J.* 567–573 (1983), which is incorporated herein by reference. In this model, the substrate is Ala-7-amido-4-methylcoumarin (hereafter "Ala-AMC"). Ala-AMC (non-fluorescent), which is known to be degraded by aminopeptidase to yield the metabolites Ala and AMC (AMC is fluorescent), is used to determine potency of putative enkephalin-degrading enzyme inhibitors. More specifically, a test sample (containing substrate, putative inhibitor and aminopeptidase) and control sample (containing substrate and aminopeptidase only) are incubated. Fluorescence by the metabolite in each sample is measured. If the test sample is found to contain significantly less metabolite (i.e., demonstrates significantly less fluorescence) than the control sample, the test compound demonstrates significant in vitro inhibition of peptide degradation by an enkephalin-degrading enzyme. Accordingly, the test compound is a preferred enkephalin-degrading enzyme inhibitor.

Another model that assesses the ability of a compound to inhibit degradation by enkephalin-degrading enzyme (in this model, the enzyme is angiotensin-converting enzyme ("ACE"), a known enkephalin-degrading enzyme) is described by Fournie-Zaluski et al., "Differential Recognition of 'Enkephalinase' and Angiotensin-Converting Enzyme By New Carboxyalkyl Inhibitors", 31 *Life Sci.* 2947–54 (1982). In this model, the substrate Hip-His-Leu (a non-fluorescent substrate which is known to be degraded by ACE to yield the metabolites Hip and His-Leu (fluorescent)) is used to determine potency of putative enkephalin-degrading enzyme inhibitors. A test sample (containing substrate, putative inhibitor and ACE) and control sample (containing substrate and ACE only) are incubated. Fluorescence by the metabolite His-Leu in each sample is measured. If the test sample is found to contain significantly less metabolite (i.e., demonstrates significantly less fluorescence) than the control sample, the test compound demonstrates significant in vitro inhibition of peptide degradation by an enkephalin-degrading enzyme. Accordingly, the test compound is a preferred enkephalin-degrading enzyme inhibitor.

As indicated, preferred opioid-degrading enzyme inhibitors are those compounds that significantly inhibit in vitro peptide degradation by an enkephalin-degrading enzyme in any of the above-described, or similar, in vitro models. Particularly preferred opioid-degrading enzyme inhibitors useful in the methods of the present invention are those compounds that demonstrate significant stimulation of osteoblast-like cell proliferation in vitro, according to the model described above.

Numerous enkephalin-degrading enzyme inhibitors, and methods for their preparation, are described in the literature and are useful in the methods of the present invention. Such inhibitors are described in the following references, all of which are incorporated herein by reference: U.S. Pat. No. 4,380,535, to Sarantakis, issued Apr. 19, 1983; U.S. Pat. No. 4,423,242, to Wilkinson et al., issued Dec. 27, 1983; U.S. Pat. No. 4,474,795, to Greenberg et al., issued Oct. 2, 1984; U.S. Pat. No. 4,504,492, to Wilkinson et al., issued Mar. 12, 1985; U.S. Pat. No. 4,513,009, to Roques et al., issued Apr. 23, 1985; U.S. Pat. No. 4,514,391, to Gordon et al., issued Apr. 30, 1985; U.S. Pat. No. 4,528,296, to Vecchietti et al., issued Jul. 9, 1985; U.S. Pat. No. 4,552,866, to Delaney et al., issued Nov. 12, 1985; U.S. Pat. No. 4,567,198, to Delevallee et al., issued Jan. 28, 1986; U.S. Pat. No. 4,610,816, to Berger, issued Sep. 9, 1986; U.S. Pat. No. 4,611,002, to Ondetti, issued Sep. 9, 1986; U.S. Pat. No. 4,618,708, to Roques et al., issued Oct. 21, 1986; U.S. Pat. No. 4,636,522, to Gordon, issued Jan. 13, 1987; U.S. Pat. No. 4,670,541, to Delaney et al., issued Jun. 2, 1987; U.S. Pat. No. 4,681,960, to Kakimoto et al., issued Jul. 21, 1987; U.S. Pat. No. 4,721,726, to Berger, issued Jan. 26, 1988; U.S. Pat. No. 4,722,810, to Delaney et al., issued Feb. 2, 1988; U.S. Pat. No. 4,939,261, to Ksander, issued Jul. 3, 1990; U.S. Pat. No. 5,096,925, to Ksander, issued Mar. 17, 1992; U.S. Pat. No. 5,098,934, to Vevert et al., issued Mar. 24, 1992; U.S. Statutory Invention Registration No. H642, Floyd et al., published Jun. 6, 1989; United Kingdom Patent Publication 8111322, Wilkinson, published Nov. 4, 1981; United Kingdom Patent Publication, Wilkinson et al., published Apr. 7, 1983; European Patent Publication 161,769, Delaney et al., published Nov. 21, 1985; European Patent Publication 341,081, Kawamura et al., published Nov. 8, 1989; European Patent Publication 474,553, Shibahara et al., published Mar. 11, 1992; PCT Patent Publication 92/03410, Neustadt et al., published Mar. 5, 1992; Fournie-Zaluski et al., "Differential Recognition of 'Enkephalinase' and Angiotensin-Converting Enzyme by New Carboxyalkyl Inhibitors", 31 *Life Sci.* 2947–2954 (1982); Mimura et al., "A Novel Class of Enkephalinase Inhibitors Containing a C-Terminal Sulfo Group", 35 *J. Med. Chem.* 602–608 (1992).

Preferred enkephalin-degrading enzyme inhibitors useful in the methods of the present invention have the general structure of formula (I):

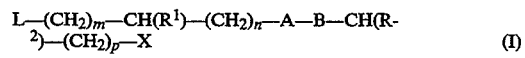

$$L-(CH_2)_m-CH(R^1)-(CH_2)_n-A-B-CH(R^2)-(CH_2)_p-X \qquad (I)$$

wherein
(1) L is —S—$R^3$ or —C(=O)—$R^4$; where $R^3$ is hydrogen or —C(=O)—$R^5$, where $R^5$ is lower alkyl; and where $R^4$ is hydroxy or —NHOH;
(2) $R^1$ is hydrogen, lower alkyl, aryl, arylalkyl (preferably methyl or phenylmethyl);
(3) A is —C(=O)—, —NH—C(=O)—, or —N($R^6$)—, where $R^6$ is hydrogen or lower alkyl;
(4) B is —NH—, —O—, —S—, or —C(=O)—;
(5) $R^2$ is hydrogen, lower alkyl, aryl, arylalkyl (preferably phenylmethyl);

(6) X is —C(=O)—NH—R⁷ or —C(=O)—O—R⁷, where R⁷ is hydrogen, lower alkyl, phenyl, or arylalkyl;

(7) m is from 0 to about 2;

(8) n is 0 or 1 (preferably 0); and (9) p is from 0 to about 4 (preferably 0 or 1);

and pharmaceutically-acceptable salts thereof.

Other preferred enkephalin-degrading enzyme inhibitors have the general structure:

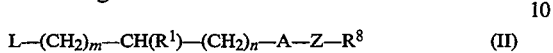

$$L\text{—}(CH_2)_m\text{—}CH(R^1)\text{—}(CH_2)_n\text{—}A\text{—}Z\text{—}R^8 \quad (II)$$

wherein:

(1) L, R¹, A, m, and n are as described in formula (I);

(2) Z is —NH—, —O—, —S—, —C(=O)—, or nil; and (3) R⁷ is a carbocyclic ring or a heterocyclic ring; preferably benzenesulfonic acid, pyridyl, or morpholinyl;

and pharmaceutically-acceptable salts thereof.

Other preferred enkephalin-degrading enzyme inhibitors, as described in U.S. Pat. No. 4,721,726, to Berger, issued Jan. 26, 1988, have the general structural formula (III):

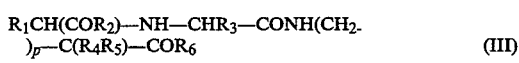

$$R_1CH(COR_2)\text{—}NH\text{—}CHR_3\text{—}CONH(CH_2\text{-})_p\text{—}C(R_4R_5)\text{—}COR_6 \quad (III)$$

and the racemates, enantiomers and diasterioisomers thereof and the phamaceutically acceptable salts thereof wherein:

$R_1$ is alkyl having from 1 to 6 carbon atoms, adamantylmethyl, cycloakylmethyl having from 4 to 8 carbon atoms or A—$X_m$—$C_nH_{2n}$— wherein X is oxygen or sulfur, A is phenyl which may be substituted with the group, Y, where i n Y is halogen, hydroxy, trifluoromethyl, alkoxy having from 1 to 6 carbon atoms, alkyl having from 1 to 6 carbon atoms, 2- and 3-furanyl, 2- and 3-thienyl, or phenyl (which may be substituted with halogen, hydroxy, trifluoromethyl, alkoxy having from 1 to 6 carbon atoms or alkyl having from 1 to 6 carbon atoms) benzyl {the phenyl ring of which may be substituted with the group, Y, as defined herein}, 1- and 2-naphthyl, 2- and 3-furanyl or 2- and 3-thienyl; m is 0 or 1 and n is 0, 1, 2, 3, or 4;

$R_2$ and $R_6$ may be the same or different and are hydroxy, alkoxy having from 1 to 8 carbon atoms, B—$X_m$—$C_nH_{2n}$—O— wherein B is phenyl (which may be substituted with the group, Y, as defined herein} or 1- and 2-naphthyl, X, m, and n are as defined herein provided that when n=0, m=0, —OCH₂OCO—alkyl having from 3 to 8 carbon atoms, —OCH₂CO-Phenyl (the phenyl ring of which may be substituted with the group, Y, as defined herein), 1-glyceryl,

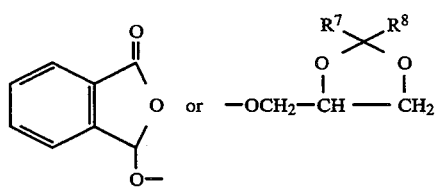

wherein R₇ is hydrogen, alkyl having from 1 to 6 carbon atoms, or phenyl which may be substituted with the group, Y, as defined herein, and R₈ is hydrogen or alkyl having from 1 to 6 carbon atoms;

R₂ may also be —NR₇R₈ wherein R₇ and R₈ are as defined herein;

R₃ is alkyl having from 1 to 6 carbon atoms, cycloalkylmethyl having from 4 to 8 carbon atoms, 2- and 3-thienylmethyl, 2- and 3-furanylmethyl, 1- and 2-naphthylmethyl, or benzyl the phenyl ring of which may be substituted with the group, Y, as defined herein;

R₄ is D—$C_nH_{2n}$—$O_m$— wherein D is hydrogen, alkyl having from 1 to 4 carbon atoms or phenyl which may be substituted with the group, Z, wherein Z is halogen, hydroxy, trifluoromethyl, alkoxy having from 1 to 6 carbon atoms, or alkyl having from 1 to 6 carbon atoms; m and n are as defined herein;

R₄ may also be —NR₅COR₇ {wherein R₅ and R₇ are defined herein}, and —NR₅CO₂R₉ {wherein R₅ is defined herein and R₉ is alkyl having from 1 to 6 carbon atoms or phenyl which may be substituted with the group Y, as defined herein} provided that p is 1 or 2;

R₅ is hydrogen or alkyl having from 1 to 6 carbon atoms; and p is 0, 1 or 2.

Other preferred enkephalin-degrading enzyme inhibitors, as described by Mimura et al., "A Novel Class of Enkephalinase Inhibitors Containing a C-Terminal Sulfo Group", 35 *J. Med. Chem.* 602–608, have the general structure:

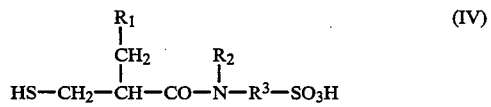

wherein:

R¹ is selected from phenyl, p-methylphenyl, p-methoxyphenyl, p-fluorophenyl, p-trifluoromethylphenyl, p-nitrophenyl, p-dimethylaminophenyl, p-phenylphenyl, phenylethyl, 1-naphytyl, 3-pyridyl, 1,2-benzisoxazol-3-yl, or 1-methylethyl;

R₂ is selected from hydrogen or cyclopropyl; and

R³ is selected from CH₂, CH₂—CH₂, CH₂—CH₂—CH₂, CH(CH₃), CH(CH₂CH(CH₃)₂), o-phenyl, m-phenyl, p-phenyl, p-phenylmethyl, and 1,4-naphthylene.

Particularly preferred enkephalin-degrading enzyme inhibitors useful in the methods of the present invention include (DL-3-mercapto-2-benzylpropanoyl)-glycine; 1-(DL-3-mercapto-2-methylpropanoyl)-L-proline; 2-benzyl-3-(N-hydroxycarboxamido)-propanoyl-L-alanine; 2-benzyl-3-(N-hydroxycarboxamido)-propanoyl-L-phenylalanine; (±)-N-(2-acetylthio)methyl-1-oxo-3-phenylpropyl glycine benzyl ester; N-morpholinyl-2-phenylmethyl-3-mercaptopropanamide; alpha-(mercaptomethyl)-N-(4-pyridyl)benzenepropanamide; N-[2-benzyl-3-(N-hydroxycarboxamido)-propanoyl]-3-amino-4-phenylbutyric acid; N-[(R,S)-2-benzyl-3-[(S)(2-amino-4-methylthio)butyldithio]-1-oxopropyl]-L-Phe-benzyl ester; N-(2-benzyl-3-mercaptopropanoyl) metanilic acid; and N-[(R,S)-2-carboxy-3-phenylpropanoyl]-L-Leu.

Enkephalin Secretagogues

Among the methods of this invention is administration of "enkephalin secretagogues". As referred to herein, the term "enkephalin secretagogue" includes any compound that increases (stimulates) in vivo enkephalin release (secretion).

Preferred enkephalin secretagogues are those compounds that significantly stimulate in vitro release of enkephalin. In vitro release of enkephalin can be determined using any of several art-recognized in vitro models. One such model is described by Rosen et al., "Regulated Expression of Proenkephalin A in Normal Lymphocytes", 143 *J. Immunol.* 3703-07 (1989), which is incorporated herein by reference. In this model, "target cells" (preferably bone-derived cells, such as human osteoblast-like cells, rat calvaria cells, rat osteosarcoma cells, etc.) are incubated in tissue culture medium in the presence (test sample) and absence (control sample) of a test agent. After incubation, routine radioimmuno assay ("RIA") is performed on each sample to measure the amount of a specific enkephalin (e.g., leu-enkephalin, met-enkephalin) present in each sample: If the test sample is shown to significantly stimulate in vitro release of enkephalin, the test compound is a preferred enkephalin secretagogue.

Particularly preferred enkephalin secretagogues are those compounds that stimulate enkephalin release, and demonstrate significant stimulation of osteoblast-like cell proliferation in vitro. A particularly preferred enkephalin secretagogue is the peptide Tyr-Arg.

METHODS OF TREATMENT

The present invention provides methods of treatment of osteoporosis in a human or other animal subject, comprising administering to said subject a safe and effective amount of a compound selected from opioids, opioid-degrading enzyme inhibitors, enkephalin secretagogues, and mixtures thereof. A preferred method comprises administering from about 0.05 mg/kg/day to about 5.0 mg/kg/day of an opioid. A preferred method of administering an opioid comprises administering from about 0.05 mg/kg/day to about 5.0 mg/kg/day of an enkephalin. Another preferred method comprises administering from about 0.05 mg/kg/day to about 10.0 mg/kg/day of-an enkephalin secretagogue. Another preferred method of the present invention comprises administering from about 0.1 mg/kg/day to about 10.0 mg/kg/day of an opioid-degrading enzyme inhibitor. A particularly preferred method comprises administering from about 0.1 mg/kg/day to about 10.0 mg/kg/day of an enkephalin-degrading enzyme inhibitor.

A preferred method of administration comprises administering to a subject a safe and effective amount of an active selected from the group consisting of opioids, opioid-degrading enzyme inhibitors, enkephalin secretagogues, and mixtures thereof, wherein the active is administered in a cyclical regimen comprising a cycle that is repeated one or more times, the cycle comprising
  (a) at least one active period of one or more days during which one or more of the actives are administered daily; and
  (b) at least one non-active period of one or more days during which no active is administered.

During either the active and/or the non-active periods of a given cycle, calcium and/or other agents (e.g. Vitamin $D_3$) can be administered to, among other things, improve calcium balance. Also, as discussed below, other agents such as bone loss inhibitors can be administered during the active and/or the non-active periods of a given cycle. As referred to herein, a "non-active agent" is an agent that is not an active, as that term is defined above. Examples of non-active agents are calcium Vitamin $D_3$, phosphonate, estrogen hormone, calcitonin, etc.

From the above definition, numerous "cycles" (and "cyclical regimens") are within the scope of the present invention. For example, a cycle may consist of a non-active period, followed by an active period, followed by an non-active period. Also, a cycle may consist of an active period, followed by a non-active period, followed by an active period. With those cycles comprising more than one non-active period, different non-active agents can be administered during the respective non-active periods. That is, during the first non-active period a non-active agent such as a bone-loss inhibitor may be administered alone or with a nutritional supplement. During the second non-active period of that cycle, calcium alone, bone-loss inhibitor alone, no agent, etc. may be administered. Similarly, during the active period, the active(s) can be administered alone or together with non-active agents. Where a cycle consists of more than one active period, the individual active periods may be the same or different. For example, in the first active period, an active may be administered alone. During the second active period, the active may be administered with a non-active agent. Also, different actives may be administered during different active periods of the same cycle.

An example of a cyclical regimen is where the cycle comprises one or more days during which an active is administered (active period), followed by a non-active period of one or more days during which no active is administered, with repetition of the cycle. Another such cyclical regimen comprises administering an enkephalin for about seven days (active period), followed by a non-active period of about seven days, with repetition of the cycle. A preferred cyclical regimen comprises administering an enkephalin-degrading enzyme inhibitor for from about 10 days to about 40 days (preferably about 28 days) (active period), followed by a non-active period of from about 10 to about 40 days (preferably for about 28 days) where from about 500 to about 1000 grams of calcium per day is administered, with repetition of the cycle.

A specific active within a given class of actives may be administered in combination with an active of another class of actives. Thus, for example, an enkephalin-degrading enzyme inhibitor may be administered concurrently with an enkephalin. One such method includes administering the combination of from about 0.1 mg/kg/day to about 10.0 mg/kg/day of an enkephalin-degrading enzyme inhibitor and from about 0.05 mg/kg/day to about 5.0 mg/kg/day of an enkephalin. Similarly, a plurality of actives of a given class of actives may be administered in combination. One such method includes administration of from about 0.1 mg/kg/day to about 10.0 mg/kg/day of two (2) enkephalin-degrading enzyme inhibitors. Preferably, the inhibitors would each demonstrate inhibitory potency against a different enkephalin-degrading enzyme inhibitor. For example, one inhibitor demonstrates potency against an "enkephalinase" enzyme, while the other inhibitor demonstrates potency against an "aminopeptidase" enzyme.

A combination of actives may also be administered in a cyclical regimen. One such cyclical regimen includes administering a combination of from about 0.1 mg/kg/day to about 10.0 mg/kg/day of an enkephalin-degrading enzyme inhibitor and from about 0.05 mg/kg/day to about 5.0 mg/kg/day of an enkephalin for one or more days (active period), followed by a non-active period of one or more days during which no actives are administered, with repetition of the cycle. Again, non-active agents, such as calcium, may be administered during the non-active period.

The actives useful in the methods of the present invention may also be administered in combination with agents that are known in the art to be bone loss inhibitors. One such class of bone loss inhibitors are the phosphonates, particularly the bisphosphonates. Bisphosphonates useful in the methods of this invention and methods for making such compounds, are described in the following patent documents, all incorporated by reference herein: U.S. Pat. No. 3,553,314, Francis, issued Jan. 5, 1971; U.S. Pat. No. 3,683,080, Francis, issued Aug. 8, 1972; U.S. Pat. No. 3,846,420, Wollmann et al., issued Nov. 5, 1974; U.S. Pat. No. 3,899,496, Schindler et al., issued Aug. 12, 1975; U.S. Pat. No. 3,941,772, Ploger et al., issued Mar. 2, 1976; U.S. Pat. No. 3,957,160, Ploger et al., issued May 18, 1976; U.S. Pat. No. 3,962,432, Schmidt-Dunker, issued Jun. 8, 1976; U.S. Pat. No. 3,979,385, Wollmann et al., issued Sep. 7, 1976; U.S. Pat. No. 3,988,443, Ploger et al., issued Oct. 26, 1976; U.S. Pat. No. 4,054,598, Blum et al., issued Oct. 18, 1977; U.S. Pat. No. 4,113,861, Fleisch et al., issued Sep. 12, 1978; U.S. Pat. No. 4,117,090, Ploger, issued Sep. 26, 1978; U.S. Pat. No. 4,134,969, Schmidt-Dunker, issued Jan. 16, 1979; U.S. Pat. No. 4,267,108, Blum et al., issued May 12, 1981; U.S. Pat. No. 4,304,734, Jary et al., issued Dec. 8, 1981; U.S. Pat. No. 4,330,537, Francis, issued May 18, 1982; U.S. Pat. No. 4,407,761, Blum et al., issued Oct. 4, 1983; U.S. Pat. No. 4,469,686, Andrews, issued Sep. 4, 1984; U.S. Pat. No. 4,578,376, Rosini, issued Mar. 25, 1986; U.S. Pat. No. 4,608,368, Blum et al., issued Aug. 26, 1986; U.S. Pat. No. 4,621,077, Rosini et al., issued Nov. 4, 1986; U.S. Pat. No. 4,687,767, Bosies et al., issued Aug. 18, 1987; U.S. Pat. No. 4,687,768, Benedict et al., issued Oct. 18, 1987; U.S. Pat. No. 4,711,880, Stahl et al., issued Dec. 8, 1987; U.S. Pat. No. 4,719,203, Bosies et al., issued Jan. 12, 1988; U.S. Pat. No. 4,927,814, Gall et al., issued May 22, 1990; U.S. Pat. No. 4,990,503, Isomura et al., issued Feb. 5, 1991; German Offenlegungsschrift 2,104,476, Worms, published Aug. 17, 1972; German Offenlegungsschrift 2,343,147, Ploeger et al., published Apr. 3, 1975; German Offenlegungsschrift 2,360,798, Worms et al., published Jun. 26, 1975; German Offenlegungsschrift 2,513,966, Schmidt-Dunker, published Oct. 7, 1976; German Offenlegungsschrift 2,541,981, Eimers et al., published Mar. 24, 1977; German Offenlegungsschrift 3,334,211, Blum, published Apr. 4, 1985; Japanese Patent Publication 78/59,674, Suzuki et al., published May 29, 1978; Japanese Patent Publication 79/135,724, Suzuki et al., published Oct. 22, 1979; Japanese Patent Publication 80/98193, Suzuki et al., published Jul. 25, 1980; European Patent Publication 88,359, Blum et al., published Sep. 14, 1983; European Patent Publication 100,718, Breliere et al., published Feb. 15, 1984; European Patent Publication 186,405, Benedict et al., published Jul. 2, 1986; European Patent Publication 197,478, Bosies et al., published Oct. 15, 1986; European Patent Publication 230,068, Benedict et al., published Jul. 29, 1987; European Patent Publication 273,514, Ebetino et al., published Jul. 6, 1988; European Patent Publication 274,158, Ebetino et al., published Jul. 13, 1988; European Patent Publication 282,309, Sakamoto et al., published Sep. 14, 1988; European Patent Publication 282,320, Isomura et al., published Sep. 14, 1988; PCT Patent Publication 87/03598, Binderup et al., published Jun. 18, 1987; and PCT Patent Publication 88/00590, Gall et al., published Jan. 28, 1988.

The bisphosphonates and specific active(s) of the present invention can be administered either sequentially or concurrently, preferably concurrently. A preferred method comprises concurrent, daily administration of a combination of about 1.0 LED of a bisphosphonate and from about 0.1 mg/kg/day to about 10.0 mg/kg/day of an enkephalin-degrading enzyme inhibitor. Another preferred method comprises concurrent, daily administration of a combination of about 1.0 LED of a bisphosphonate, from about 0.05 mg/kg/day to about 5.0 mg/kg/day of an enkephalin, and from about 0.1 mg/kg/day to about 10.0 mg/kg/day of an enkephalin-degrading enzyme inhibitor. A preferred sequential method comprises administering about 1.0 LED of bisphosphonate daily for two (2) weeks, followed by daily administration of from about 0.1 mg/kg to about 10.0 mg/kg of an enkephalin-degrading enzyme inhibitor for four (4) weeks.

The use of an active (or actives) of the present invention with a bisphosphonate can be administered in a cyclical regimen. One such method comprises daily administration of a combination of about 1.0 LED of a bisphosphonate and an active (preferably from about 0.1 mg/kg/day to about 10.0 mg/kg/day of an enkephalin-degrading enzyme inhibitor) for one or more days (active period), followed by a non-active period of one or more days where no combination is administered, with repetition of the cycle. Another such method comprises daily administration of a combination of about 1.0 LED of a bisphosphonate, from about 0.05 mg/kg/day to about 5.0 mg/kg/day of an enkephalin, and from about 0.1 mg/kg/day to about 10.0 mg/kg/day of an enkephalin-degrading enzyme inhibitor for one or more days (active period), followed by one or more days where no combination is administered (non-active period), with repetition of the cycle. Another such cyclical method comprises administering about 1.0 LED of bisphosphonate daily for from about 5 days to about 25 days (preferably about two (2) weeks) (first non-active period), followed by daily administration of an active (preferably from about 0.1 mg/kg to about 10.0 mg/kg of an enkephalin-degrading enzyme inhibitor) for from about 20 days to about 40 days (preferably about four (4) weeks) (active period), followed by a period of from about 20 days to about 40 days (preferably about four (4) weeks) during which no bisphosphonate or active is administered (second non-active period) (preferably calcium is administered during this second non-active period).

Another class of compounds known to be bone loss inhibitors are the estrogen hormones. As referred to herein, an "estrogen hormone" refers to naturally occurring hormones, synthetic steroidal compounds, and non-steroidal compounds, and conjugates, metabolites and derivatives thereof, which having estrogenic activity. Naturally-occurring estrogen hormones are steroids which contain a cyclopentanoperhydrophenathrene ring system. Such naturally-occurring estrogen hormones are obtained from pregnant mares' urine or prepared synthetically, using methods well-known in the art. See: "Estrogens", *Drug Information* 1765 (1990); and Rudy, "Hormone Replacement Therapy—How to Select the Best Preparation and Regimen," 88 *Postgraduate Medicine* 157 (1990) ; and C. Christiansen et al., "Estrogens, Bone Loss and Prevention," 1 *Osteoporosis Int.* 7 (1990); all of which are incorporated by reference herein.

Estrogen hormones useful in the methods of this invention include, for example, estradiol, estrone, estriol, equilin, equilenin, estradiol cypionate, estradiol valerate, ethinyl estradiol, polyestradiol phosphate, estropipate, diethylstilbestrol, dienestrol, chlorotrianisene, and mixtures thereof. A preferred estrogen hormone useful herein is "conjugated estrogen", which is a mixture of sodium salts of the water-soluble sulfate esters of estrone and equilin. Such conjugated estrogens may also contain other estrogenic substances found in pregnant mares' urine, such as 17-α-dihydroequiline, 17-α-estradiol, equilenin, and 17-α-dihydroequilenin.

An estrogen hormone and specific active(s) of the present invention can be administered either sequentially or concurrently, preferably concurrently. A preferred method comprises concurrent, daily administration of from about 0.30 mg/day to about 1.25 mg/day (preferably about 0.625 mg/day) of conjugated estrogen and from about 0.1 mg/kg/day to about 10.0 mg/kg/day of an enkephalin-degrading enzyme inhibitor.

Another preferred method comprises concurrent, daily administration of an estrogen hormone and an active (or actives) of the present invention in a cyclical regimen. One such preferred cyclical regimen comprises daily administration of from about 0.30 mg/day to about 1.25 mg/day (preferably about 0.625 mg/day) of conjugated estrogen and an active (preferably from about 0.1 mg/kg/day to about 10.0 mg/kg/day of an enkephalin-degrading enzyme inhibitor) for from about 10 days to about 40 days (preferably for about 25 days) (active period), followed by a non-active period of of from about 3 days to about 20 days (preferably for about 5 days) during which no estrogen or active is administered (preferably, 2.5 mg/day of medroxyprogesterone is administered during the non-active period), with repetition of the cycle. Calcium and other nutritional agents (e.g., Vitamin D$_3$) can also be administered during the non-active period to improve calcium balance. Another cyclical regimen comprises administering concurrently from about 0.30 mg/day to about 1.25 mg/day (preferably about 0.625 mg/day) of conjugated estrogen, from about 0.1 mg/kg/day to about 10.0 mg/kg/day of an enkephalin-degrading enzyme inhibitor, and from about 0.05 mg/kg/day to about 5.0 mg/kg/day of an enkephalin for from about 10 days to about 40 days (preferably for about 25 days) (activeperiod), followed by a non-active period of from about 3 days to about 20 days (preferably for about 6 days) during which no estrogen, enkephalin, nor inhibitor is administered, with repetiton of the cycle.

Another agent known to be a bone loss inhibitor is calcitonin. Naturally occurring calcitonin can be obtained from, for example, human, salmon, and eel sources. In addition, various synthetic analogs have been prepared. See J. Carstens, Jr. et al. "Future Horizans for Calcitonin: A U.S. Perspective", 49 *Calcif. Tissue Int.* (*Supp.* 2) S2-S6 (1991). As used herein, the term "calcitonin" refers to any naturally-occurring form of calcitonin, or any synthetic analog of calcitonin, that exhibits calcitonin-like bone activity. For use in the present invention, the preferred source of calcitonin salmon calcitonin, which is commercially available.

Calcitonin and specific active(s) of the present invention can be administered either sequentially or concurrently, preferably sequentially. Calcitonin and specific active(s) of the present invention are preferably administered in a cyclical regimen. One such cyclical regimen conists of a cycle comprising daily administration of about 1.0 LED of calcitonin for from about 5 days to about 25 days (preferably about two (2) weeks) (first non-active period), followed by daily administration of an active (preferably from about 0.05 mg/kg to about 5.0 mg/kg of enkephalin) for from about 20 days to about 40 days (preferably for about 4 weeks) (active period), followed daily administration of from about 500 to about 1,000 mg of calcium supplement from about 20 days to about 40 days (preferably for about 4 weeks) (second non-active period), with repetition of the cycle.

As used herein, the term "LED", or "least effective dose", is the minimum dose of bone resorption inhibitor which is effective, by itself, to cause a significant inhibition of bone resorption. (As used herein, the term "bone resorption inhibitor" refers to phosphonates, estrogen hormones, calcitonin, etc.) As with any pharmaceutically-active material, the specific LEDs of the bone resorption inhibitors will vary depending upon their chemical composition, and their method of administration (i.e., oral or parenteral). Nevertheless, the LED for specific bone resorption inhibitors useful herein may be determined using methods well known in the art.

In particular, the LEDs for calcitonin and bisphosphonate analogs may be determined using any of several art-recognized in vivo models. One such model is the thyroparathyroidectomized ("TPTX") rat model. In this model, compounds are evaluated for in vivo bone resorption inhibition potency, by measuring their ability to inhibit the increase of serum calcium levels caused by administration of parathyroid hormone in rats whose parathyroid gland has been removed. This model is described in Russell et al., 6 *Calcified Tissue Research* 183 (1970); Muhlbauer et al., 5 *Mineral Electrolite Metabolism* 296 (1981) ; U.S. Pat. No. 4,761,406, Flora et al., issued Aug. 2, 1988; and European Patent Publication 298,553, Ebetino, published Jan. 11, 1989; all of which are incorporated by reference herein.

Another model is the "Schenk Model" which measures the effects of bisphosphonates on bone growth in young rats. This model is described in Schenk et al., 11 *Calcif. Tissue Res.* 196 (1973); Shinoda et al., 35 *Calcif. Tissue Int.* 87 (1983); U.S. Pat. No. 4,761,406, Flora et al., issued Aug. 2, 1988; and European Patent Publication 298,553, Ebetino, published Jan. 11, 1989; all of which are incorporated by reference herein.

Another model is the "ovariectomized" or "OVX" rat model, which measures the ability of bisphosphonates to prevent loss of bone in female rates induced by ovariectomy. This model is described in Wronski et al., 125 *Endocrinology* 810 (1989), incorporated by reference herein.

The methods of this invention comprise treatment of osteoporosis at all stages of the disorder. Since osteoporosis is an ongoing process of bone loss, rather than a disorder having a discrete beginning- or end-point, "treatment", as referred to herein, consists of any method which stops, slows, or reverses the process of net bone loss which occurs in osteoporosis.

Preferred methods of this invention comprise treatment of osteoporosis in subjects who have already lost skeletal mass (herein referred to as "established osteoporosis"). Such methods of this invention for the treatment of established osteoporosis preferably comprise administering of the actives for a period of time sufficient to achieve an increase in the net skeletal mass of said subject. The increase in net skeletal mass may be in cortical bone, trabecular bone, or both. Preferably, the net skeletal mass is increased by at least about 1% per year, more preferably at least about 5% per year.

The specific period of time sufficient to achieve an increase in the net skeletal mass of the subject may depend on a variety of factors. Such factors include, for example, the specific actives employed, the amount of actives administered, the age and sex of the subject, the specific disorder to be treated, concomitant therapies employed (if any), the general physical health of the subject (including the presence of other disorders), the extent of bone loss in the individual, and the nutritional habits of the individual.

The methods of this invention are preferably continued for at least about six months, preferably for at least about twelve months. Of course, such administration may be continued indefinitely, according to sound medical practice. Preferably the subject is treated until a net skeletal mass is obtained that is clinically determined to be above the fracture threshold for the subject. See, B. L. Riggs et al., "Involutional Osteoporosis" 314 *New England J. of Medicine* (1986), incorporated by reference herein.

According to the methods of this invention, "administering" refers to any method which, in sound medical practice, delivers the actives used in this invention to the subject to be treated in such a manner so as to be effective in the building of bone. The actives may be administered by any of a variety of known methods of administration, e.g., orally, dermatomucosally (for example, dermally, sublingually, intranasally, and rectally), parenterally (for example, by subcutaneous injection, intramuscular injection, intra-articular injection, intravenous injection), and by inhalation. Thus, specific modes of administration include, for example, oral, transdermal, mucosal, sublingual, intramuscular, intravenous, intraperitoneal, subcutaneous administration, and topical application. A preferred mode for delivering enkephalins is intravenous administration. A preferred mode for delivering enkephalin-degrading enzyme inhibitors is orally. A preferred method of delivery for enkephalin secretagogues is intravenous administration.

A preferred method for the treatment of osteoporosis includes an initial diagnostic step, to determine the presence of the disorder. Thus, a preferred method of this invention comprises the steps of performing a diagnostic on a human subject for the detection of osteoporosis and, upon obtaining a positive result from said diagnostic, administering the actives according to the methods of this invention. Suitable diagnostics for the detection of established osteoporosis are well known in the art. Such methods include the measurement of the radiodensity of skeletal radiographs, quantitative computerized tomography, single energy photon absorptiometry, dual-energy photon absorptiometry, and duel-energy x-ray absorptiomety (DEXA). Diagnostic techniques among those useful herein are described in W. A. Peck et al., Physician's Resource Manual on Osteoporosis (1987), published by the National Osteoporosis Foundation (incorporated by reference herein).

Dosage Forms

The actives described herein may be administered in any of a variety of pharmaceutically-acceptable compositions. Such compositions may comprise an active and a pharmaceutically-acceptable carrier. Also, such compositions may comprise multiple actives (if the specific actives are capable of being administered via the same delivery route) and a pharmaceutically-acceptable carrier. Accordingly, for example, compositions for co-administering two or more actives comprise:
- (a) from about 6.0 mg to about 600.0 mg of an enkephalin-degrading enzyme inhibitor;
- (b) from about 3.0 mg to about 300 mg of an enkephalin; and
- (c) a pharmaceutically-acceptable carrier.

Compositions may also comprise an active or multiple actives, a known bone-loss inhibitor (e.g., a phosphonate or estrogen hormone), and a pharmaceutically-acceptable carrier (if all agents are capable of being administered via the same delivery route). Accordingly, for example, compositions for co-administering an active of the present invention together with estrogen comprise:
- (a) from about 6.0 mg to about 600 mg of an enkephalin-degrading enzyme inhibitor;
- (b) from about 0.30 mg to about 1.25 mg of conjugated estrogen; and
- (c) a pharmaceutically-acceptable carrier.

Similarly, compositions for co-administering multiple actives of the present invention together with a known bone-loss inhibitor comprise, for example:
- (a) from about 6.0 mg to about 600 mg of an enkephalin-degrading enzyme inhibitor;
- (b) from about 3.0 mg to about 300 mg of an enkephalin;
- (c) from about 0.30 mg to about 1.25 mg of conjugated estrogen; and
- (d) a pharmaceutically-acceptable carrier.

Pharmaceutically-acceptable carriers include solid or liquid filler diluents or encapsulating substances, and mixtures thereof, that are suitable for administration to a human or lower animal. The term "compatible", as used herein, means that the components of the pharmaceutical composition are capable of being commingled with the actives, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of the substances which can serve as pharmaceutical carriers are: sugars, such as lactose, glucose and sucrose; starches, such as corn starch and potato starch; cellulose and its derivatives, such as sodium carboxymethylcellulose, ethylcellulose, cellulose acetate; powdered tragacanth; malt; gelatin; talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; phosphate buffer solutions; wetting agents and lubricants such as sodium lauryl sulfate; coloring agents; flavoring agents; and preservatives. Other compatible pharmaceutical additives and actives may be included in the pharmaceutically-acceptable carrier for use in the compositions of the present invention.

The choice of a pharmaceutically-acceptable carrier to be used in conjunction with the active is determined by the way the active is to be administered. If the active is to be injected, the preferred pharmaceutical carrier is sterile water, physiological saline, or mixtures thereof. The pH of such parenteral composition is preferably adjusted to about 7.4. Suitable pharmaceutically-acceptable carriers for topical application include those known in the art for use in creams, gels, tapes, patches, and similar topical delivery means.

The pharmaceutically-acceptable carrier employed in conjunction with the actives is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 5% to about 80%, and most preferably from about 10% to about 50%.

As indicated, the preferred method of administering actives is dependent upon the class of active being administered. For the enkephalin-degrading enzyme inhibitors, the preferred method of administration is orally, in a unit-dosage form (i.e., a dosage form containing an amount of active suitable for administration in one single dose, according to sound medical practice). Preferred unit dosage forms include tablets, capsules, suspensions, and solutions, comprising a safe and effective amount of active. Pharmaceutically-acceptable carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art. Preferably, oral unit dosage forms of the enkephalin-degrading enzyme inhibitor comprise from about 6.0 mg to about 600 mg of the inhibitor.

For the enkephalins, the preferred method of administration is intravenous injection, in a unit-dosage form (i.e., a dosage form containing an amount of active suitable for administration in one single dose, according to sound medical practice). Preferred unit dosage forms include suspensions and solutions, comprising a safe and effective amount of enkephalin. Pharmaceutically-acceptable carriers suitable for the preparation of unit dosage forms for intravenous administration are well known in the art. Their selection will depend on secondary considerations like cost and shelf stability, which are not critical for the purposes of the present invention, and can be made without difficulty by a person skilled in the art. Preferably, intravenous unit dosage forms of the enkephalin comprise from about 3.0 mg to about 300 mg of the enkephalin.

For the enkephalin secretagogues, the preferred method of administration is intravenous administration, in a unit-dosage form (i.e., a dosage form containing an amount of active suitable for administration in one single dose, according to sound medical practice). Preferred unit dosage forms include suspensions and solutions, comprising a safe and effective amount of enkephalin secretagogue. Pharmaceutically-acceptable carriers suitable for the preparation of unit dosage forms for intravenous administration are well known in the art. Their selection will depend on secondary considerations like cost and shelf stability, which are not critical for the purposes of the present invention, and can be made without difficulty by a person skilled in the art. Preferably, intravenous unit dosage forms of the enkephalin secretagogues comprise from about 3.0 mg to about 600 mg of the secretagogue.

Kits

This invention also provides kits for conveniently and effectively implementing the methods of this invention. Such kits comprise one or more unit doses of the active to be administered, and a means for facilitating compliance with methods of this invention. Where multiple actives will be co-administered in a single dose form, such kits comprise one or more unit doses of the combination of the actives, and a means for facilitating compliance with methods of this invention. Where actives will be co-administered, but not via a single dose form, such kits comprise one or more unit doses of each of the actives, and a means for facilitating compliance with methods of this invention.

The kits described herein may also include unit doses that contain non-active agents (e.g., phosphonate, estrogen, calcitonin, calcium, or Vitamin D 1,25). As with the actives, the contents of such kits will depend on the compatibility of delivery routes of the particular actives and agents being administered.

Such kits provide a convenient and effective means for assuring that the subject to be treated takes the appropriate active(s) in the correct dosage in the correct manner. Such kits are particularly preferred in methods of this invention which employ cyclical regimens for administration of individual or multiple actives.

The compliance means of such kits includes any means which facilitates administering the actives according to a method of this invention. Such compliance means includes instructions, packaging, and dispensing means, and combinations thereof. Examples of packaging and dispensing means are well known in the art, including those described in U.S. Pat. No. 4,761,406, to Flora et al., issued Aug. 2, 1988; U.S. Pat. No. 4,812,311, to Uchtman, issued Mar. 14, 1989; and U.S. Pat. No. 4,889,238, to Batchelor, issued Dec. 26, 1989, all of which are incorporated by reference herein.

The following non-limiting examples illustrate the compositions and methods of use of the present invention.

EXAMPLE 1

The compound DL-3-mercapto-2-benzyl-propanoylglycine[1] is screened for inhibitory activity against the peptidase "enkephalinase". Specifically, osteoblast-like cells are plated in tissue culture medium at $4 \times 10^4$ cells/well in 24-well plates in Dulbecco's Modified eagle's Medium supplemented with 5% (v/v) Fetal Bovine Serum. After 48 hrs., the cells are rinsed twice with phosphate buffered saline. A measured volume of assay buffer (50 mM HEPES, 100 mM sodium chloride, pH 7.4) is added to each well. To one series of wells a maximally active concentration ($10^{-6}$M) of DL-3-mercapto-2-benzyl-propanoylglycine is added to each well. This row of wells serves as an experimental blank to allow correction for endogenous fluorescence of the substrate and non-specific (i.e., non-enkephalinase mediated) cleavage of the substrate. The putative enkephalinase inhibitor DL-3-mercapto-2-benzyl-propanoylglycine is added to the other rows. One row is not treated with the putative inhibitor, and is used as a control group. The reaction is started by addition of N-succinyl-alanyl-alanylphenylalanyl-7-amido-4-methyl coumarin, which serves as the substrate for the enkephalinase enzyme. The cells are incubated at 37° C. for one hr. The reaction is then terminated by addition of DL-3- mercapto-2-benzyl-propanoyl-glycine ($10^{-6}$M final concentration) and the cells are incubated at 95° C. for 15 minutes. The supernatant from the cells is then placed in glass tubes and Amino-peptidase (0.75 μg/ml final concentration [pre-incubated at 56° C. for one hr]) is added. The combination is incubated at 56° C. for one hr followed by incubation at 95° C. for 15 minutes. Cleavage of the substrate by enkephalinase is monitored by measuring the fluorescence of the samples (caused by the metabolite AMC) at 440 nm following excitation at 367 nm. Enzyme activity is quantified by reference to a standard curve produced by incubation of the substrate with Thermolysin for one hr, followed by treatment in the same manner as the experimental samples. The curve is then serially diluted and the fluorescence determined for each concentration of product.

Enzyme activities are then corrected for the protein content of the individual experimental wells. Cells in each well are solublized using 0.1% (v/v) Triton X 100. An aliquot of the cell lysate is incubated (5 min.) with a protein dye binding reagent, as descibed by M. Bradford, "A Rapid and Sensitive Method for the Quantitation of Microgram Quantities of Protein Utilizing the Principle of Protein Dye Binding", 72 *Anal. Biochem.* 248–254. Absorbance of the sample is read at 595 nm using a spectrophotometer. Protein content is quantified by reference to a standard curve produced by incubation of a known concentration of a protein standard (bovine immunoglobulin G) with the dye.

The sample containing putative inhibitor is found to exhibit significantly less fluorescence, indicating that the putative inhibitor has significantly inhibited substrate degradation by enkephalinase. The test compound is therefore an "enkephalin-degrading enzyme inhibitor".

The enkephalin-degrading enzyme inhibitor DL-3-mercapto-2-benzyl-propanoylglycine is then screened to determine whether the inhibitor stimulates [$^3$H]-thymidine incorporation by osteoblast-like cells, indicating that the compound stimulates proliferation of osteoblast cells. Rat osteoblast-like cells (ROS 17/2.8) are plated at $4 \times 10^3$ cells/well in a 96-well plate in Dulbecco's Modified eagle's Medium supplemented with 2% (v/v) Fetal Bovine Serum, and incubated for 6 hrs. Control (serum-free) medium and test medium (test sample and serum-free medium) are then added to the cells and this combination is incubated for 18 hrs. The cells are then pulsed with [$^3$H]-thymidine (1 μCi/well) for 2 hrs. The medium is then removed, the cells are harvested onto glass fibre filters and the amount of [$^3$H]-thymidine (counts per minute per well) incorporated into DNA is then determined using a direct beta counter. Values for control groups are then compared to values for treated groups. The treated groups are found to exhibit significantly greater radioactivity than the control groups, indicating the test compound has significantly stimulated proliferation of the osteoblast-like cells.

A human female subject weighing about 60 kg (132 lbs), suffering from postmenopausal osteoporosis, is treated by a method of this invention. Specifically, for two years, the enkephalin-degrading enzyme inhibitor DL-3-mercapto-2-benzylpropanoylglycine is administered orally, in a cyclical regimen, where each cycle consists of an active period of 28 days during which a tablet containing 160 mg of said inhibitor is administered each day, followed by a non-active period of 28 days during which the subject receives a daily supplement of calcium (1,000 mg/day), with repeat of cycle.

The density of the subject's vertebrae is then measured by dual-energy photon absorptiometry, indicating an increase in bone mass. [1]: sold by Sigma Chemical Co. under the name "thiorphan".

EXAMPLE 2

The compound H-Tyr-D-Ala-Gly-Phe-D-Leu-OH ("DADLE") is screened according to the method described by Goldstein et al., to determine whether it exhibits significant in vitro mu opioid receptor affinity. That is, DADLE is screened to determine whether it significantly inhibits binding of radiolabeled Tyr-D-Ala-Gly-N-methyl-Phe-Gly(ol) ([$^3$H]DAGO) to mu opioid receptor binding sites. More specifically, DADLE is screened to determine whether it has an $IC_{50}$ concentration that is $\leq 1000$ times the $IC_{50}$ concentration of non-radiolabeled DAGO. DADLE is shown to exhibit significant in vitro mu opioid receptor affinity.

The compound H-Tyr-D-Ala-Gly-Phe-D-Leu-OH ("DADLE") is screened to determine whether it stimulates proliferation of osteoblast-like cells. Rat osteoblast-like cells (ROS 17/2.8) are plated at $4 \times 10^{-3}$ cells/well in a 96-well plate in Dulbecco's Modified eagle's Medium supplemented with 2% (v/v) Fetal Bovine Serum, and incubated for 6 hrs. Control sample (serum-free medium) and test sample (enkephalin and serum-free medium) are then added to the cells and this combination is incubated for 18 hrs. The cells are then pulsed with $^3$H-thymidine (1 μCi/well) for 2 hrs. The medium is then removed, the cells are harvested onto glass fibre filters, and the amount of $^3$H-thymidine (counts per minute per well) incorporated into DNA is determined using a direct beta counter. Values for control groups are then compared to values for treated groups. The treated groups are found to exhibit significantly greater radioactivity than the control groups, indicating that DADLE has significantly stimulated proliferation of the osteoblast-like cells.

A human female subject weighing about 60 kg (132 lbs), suffering from postmenopausal osteoporosis, is treated by a method of this invention. Specifically, for two years, the compound H-Tyr-D-Ala-Gly-Phe-D-Leu-OH ("DADLE") is administered to the subject, in a cyclical regimen, where each cycle consists of an active period of 28 days during which a solution containing 30 mg of DADLE is administered intravenously every day, followed by a non-active period of 28 days during which the patient receives a daily supplement of calcium (1,000 mg/day), with repeat of cycle.

The density of the subject's vertebrae is then measured by dual-energy photon absorptiometry, indicating an increase in bone mass. [1]: available from Peninsula Labs, Belmont Calif.

EXAMPLE 3

The compound Tyr-D-Cys(S-t-butylthioether)-Gly-Phe-Leu-Thr(O-t-butylether)[1] ("BUBUC") is screened according to the method described by Goldstein et al., to determine whether it exhibits significant in vitro delta opioid receptor affinity. That is, BUBUC is screened to determine whether it significantly inhibits binding of radiolabeled H-Tyr-D-Pen-Gly-Phe-D-Pen-OH ("[$^3$H]DPDPE") to delta opioid receptor binding sites. More specifically, BUBUC is screened to determine whether it has an $IC_{50}$ concentration that is $\leq 1000$ times the $IC_{50}$ concentration of non-radiolabeled DPDPE. BUBUC is shown to exhibit significant in vitro delta opioid receptor affinity.

The compound Tyr-D-Cys(S-t-butylthioether)-Gly-Phe-Leu-Thr(O-t-butylether) ("BUBUC") is screened to determine whether it stimulates proliferation of osteoblast-like cells. Rat osteoblast-like cells (ROS 17/2.8) are plated at $4 \times 10^{-3}$ cells/well in a 96-well plate in Dulbecco's Modified eagle's Medium supplemented with 2% (v/v) Fetal Bovine Serum, and incubated for 6 hrs. Control sample (serum-free medium) and test sample (BUBUC and serum-free medium) are then added to the cells and this combination is incubated for 18 hrs. The cells are then pulsed with $^3$H-thymidine (1 $\mu$Ci/well) for 2 hrs. The medium is then removed, the cells are harvested onto glass fibre filters, and the amount of $^3$H-thymidine (counts per minute per well) incorporated into DNA is determined using a direct beta counter. Values for control groups are then compared to values for treated groups. The treated groups are found to exhibit significantly greater radioactivity than the control groups, indicating that BUBUC has significantly stimulated proliferation of the osteoblast-like cells.

A human female subject weighing about 60 kg (132 lbs), suffering from postmenopausal osteoporosis, is treated by a method of this invention. Specifically, for two years, an enkephalin of the formula Tyr-D-Cys(S-t-butylthioether)-Gly-Phe-Leu-Thr(O-t-butylether) ("BUBUC") is administered to the subject, in a cyclical regimen, where each cycle consists of an active period of 28 days during which a solution containing 30 mg of BUBUC is intravenously administered each day, followed by a non-active period of 28 days during which the patient receives a daily supplement of calcium (1,000 mg/day), with repeat of cycle.

The density of the subject's vertebrae is then measured by dual-energy photon absorptiometry, indicating an increase in bone mass. In this example, the following enkephalins, among others, are substituted for Tyr-D-Cys(S-t-butylthioether)-Gly-Phe-Leu-Thr(O-t-butylether), at comparable levels, with substantially similar results: H-Tyr-D-Ser(O-t-butylether)-Gly-Phe-Leu-Thr(O-t-butylether); H-Tyr-D-Pen-Gly-Phe-Pen; H-Tyr-D-Ser(O-t-butylether)-Gly-Phe-Leu-Thr; H-Tyr-D-Ala-Gly-N-methyl-Phe-Met(sulfoxide)(ol); H-Tyr-D-Ala-Gly-Phe-D-Leu; H-Tyr-D-Ala-Gly-Phe-Leu-NH$_2$; H-Tyr-D-Ala-Gly-Phe-Met-NH$_2$; H-Tyr-D-Ala-Phe-Met-NH$_2$; H-Tyr-D-Met(O)-Gly-Phe(ol); H-Tyr-D-Met-Gly-Phe-Pro-NH$_2$; H-(2,6-dimethyl-Try)-D-Ala-NH-phenylpropyl. [1]: Prepared by the method described by Gacel et al., "Synthesis, Biochemical and Pharmacological Properties of BUBUC, a Highly Selective and Systemically Active Agonist for In Vivo Studies of Delta-Opioid Receptors", 11 *Peptides* 983–988 (1990).

EXAMPLE 4

The putative enkephalin secretagogue Tyr-Arg[1] is screened to determine whether it demonstrates significant in vitro stimulation of enkephalin secretion from osteoblast-like cells. Osteoblast-like cells are incubated in tissue culture medium in the presence (test samples) and absence of the compound Tyr-Arg for 48 hrs. Peptides are extracted from packed cells by homogenization in 10 volumes of 0.2M HCl, heated to 100° C. for 3 min. and centrifuged at 15,000×g for 30 min. at 4° C. An aliquot of the resulting supernatant is purified on a $C_{18}$ octadecyl Ampere minicolumn using a non-polar extraction procedure as recommended by the manufacturer of the columns. Another portion of the supernatant is lyophilized and reconstituted in 1.0 ml of 50 mM Tris-HCl (pH 8.0), 2 mM $CaCl_2$ containing 20 g/ml trypsin L-p-tosylamino-2-phenylethyl chloromethyl ketone. After trypsin digestion (2 hr at 3° C.), samples are heated to 100° C. for 20 min., cooled and then treated with carboxypeptidaseB (0.2 $\mu$g/ml) for 1 hr. at 37° C. After digestion, the enzyme is heat inactivated and the sample is purified on a the $C_{18}$ minicolumn described above. The purified digest is then assayed for immunoreactive enkephalin using commercially available RIA techniques according to the procedures recommended by the manufacturers (e.g., Peninsula Laboratories, Belmont, Calif.). The samples containing test compound (Tyr-Arg) are found to contain significantly more immunoreactive enkephalin, indicating that Tyr-Arg stimulates enkephalin secretion by osteoblast-like cells.

The enkephalin secretagogue Tyr-Arg is screened to determine whether it stimulates proliferation of osteoblast-like cells. Rat osteoblast-like cells (ROS 17/2.8) are plated at $4 \times 10^{-3}$ cells/well in a 96-well plate in Dulbecco's Modified eagle's Medium supplemented with 2% (v/v) Fetal Bovine Serum, and incubated for 6 hrs. Control sample (serum-free medium) and test sample (Tyr-Arg and serum-free medium) are then added to the cells and this combination is incubated for 18 hrs. The cells are then pulsed with $^3$H-thymidine (1 $\mu$Ci/well) for 2 hrs. The medium is then removed, the cells are harvested onto glass fibre filters, and the amount of $^3$H-thymidine (counts per minute per well) incorporated into DNA is determined using a direct beta counter. Values for control groups are then compared to values for treated groups. The treated groups are found to exhibit significantly greater radioactivity than the control groups, indicating that Tyr-Arg has significantly stimulated proliferation of the osteoblast-like cells.

A human female subject weighing about 60 kg (132 lbs), suffering from postmenopausal osteoporosis, is treated by a method of this invention. Specifically, for two years, the enkephalin secretagogue Tyr-Arg[1], is administered to the subject, in a cyclical regimen, where each cycle consists of an active period of 28 days during which a solution containing 30 mg of Tyr-Arg is intravenously administered each day, followed by a non-active period of 28 days during which the subject receives a daily supplement of calcium (1,000 mg/day), with repeat of cycle. The density of the subject's vertebrae is then measured by dual-energy photon absorptiometry, indicating an increase in bone mass. [1]: sold by Sigma Chemical Co. under the name "kyotorphin".

EXAMPLE 5

A human female subject weighing about 60 kg (132 lbs), suffering from postmenopausal osteoporosis, is treated by a method of this invention. Specifically, for two years, the enkephalin-degrading enzyme inhibitor DL-3-mercapto-2-benzyl-propanoylglycine[1] and the enkephalin Tyr-D-Cys(S-t-butylthioether)-Gly-Phe-Leu-Thr(O-t-butylether)[2], are concurrently administered in a cyclical regimen, where each cycle consists of a 28-day active period consisting of:

(1) daily oral administration of a tablet containing 300 mg of the enkephalin-degrading enzyme inhibitor DL-3-mercapto-2-benzyl-propanoylglycine[1]; and (2) daily intravenous administration of a solution containing 30 mg of the enkephalin Tyr-D-Cys(S-t-butylthioether)-Gly-Phe-Leu-Thr(O-t-butylether)[2], followed by a non-active period of 28 days during which the subject receives a daily supplement of calcium (1,000 mg/day), with repeat of cycle.

The density of the subject's vertebrae is then measured by dual-energy photon absorptiometry, indicating an increase in bone mass. [1]: sold by Sigma Chemical Co. under the name "thiorphan". [2]: prepared according to the method cited in Example 3.

EXAMPLE 6

A human female subject weighing about 60 kg (132 lbs) is evaluated approximately four years after spontaneous menopause, and is found to have low bone mass. The subject is then treated by a method of this invention to treat osteoporosis. Specifically, for two years, the enkephalin-degrading enzyme inhibitor DL-3-mercapto-2-benzyl-propanoylglycine[1] and conjugated estrogen are concurrently administered in a cyclical regimen, where each cycle consists of a 25-day active period consisting of:

(1) daily oral administration of a tablet containing 300 mg of the enkephalin-degrading enzyme inhibitor DL-3-mercapto-2-benzyl-propanoylglycine[1]; and (2) daily oral administration of a tablet[2] containing about 0.625 mg conjugated estrogen, followed by a non-active period of 6 days during which the subject receives medroxyprogesterone and a daily supplement of calcium (1,000 mg/day), with repeat of cycle.

The density of the subject's vertebrae is then measured by dual-energy photon absorptiometry, indicating an increase in bone mass. [1]: sold by Sigma Chemical Co. under the name "thiorphan". [2]: sold by Wyeth-Ayerst Laboratories, under the trademark "Premarin", in a carrier of calcium phosphonate tribasic, calcium sulfate anhydrous, caruauba wax, glyceryl mono-oleate, lactose, magnesium stearate, methylcellulose, microcrystalline cellulose, polyethylene glycol, stearic acid, sucrose, talc and titanium oxide.

EXAMPLE 7

A human female subject weighing about 60 kg (132 lbs), suffering from postmenopausal osteoporosis, is treated by a method of this invention. Specifically, each day for five years, the subject is administered 3 tablets, comprised as follows.

| Component | milligrams/tablet |
|---|---|
| DL-3-mercapto-2-benzyl-propanoylglycine[1] | 50.0 |
| magnesium stearate | 2.5 |
| anhydrous lactose | 172.5 |
| cross-linked polyvinyl-pyrrolidone | 25.0 |

The density of the subject's vertebrae is then measure, indicating that no significant loss in bone mass has occurred. [1]: sold under the tradename "thiorphan" by Sigma Chemical Co.

EXAMPLE 8

A human female subject weighing about 60 kg (132 lbs) is evaluated approximately four years after spontaneous menopause, and is found to have low bone mass. The subject is then treated by a method of this invention to treat osteoporosis. Specifically, once each month for five years, the subject is administered, via intravenous injection, 5 ml of a solution comprised as follows.

| Component | mg/ml |
|---|---|
| Tyr-D-Cys(S-t-butylthioether)-Gly-Phe-Leu-Thy(O-t-butylether)[1] | 30.0 |
| sodium bisulfate | 1.0 |
| sodium chloride | 7.0 |
| chlorobutanol | 5.0 |

The density of the subject's vertebrae is then measured, indicating that no significant loss in bone mass has occurred. [1]: prepared by the method cited in Example 3.

---

What is claimed is:

1. A method of treatment for osteoporosis in a human or other animal subject, comprising administering to said subject a safe and effective amount of an active selected from the group consisting of opioids, opioid-degrading enzyme inhibitors, enkephalin secretagogues, and mixtures thereof.

2. A method of treatment for osteoporosis, according to claim 1, wherein said active is an opioid.

3. A method of treatment for osteoporosis, according to claim 2, wherein said opioid is an enkephalin.

4. A method of treatment for osteoporosis, according to claim 3, wherein said enkephalin is a polypeptide having from 2 to 15 amino acids, said polypeptide comprising a polypeptide of the formula:

R-A-B-C-D-E-F-G-H-R$^1$ wherein
(1) R is hydrogen or lower alkyl;
(2) A is Tyr, 2,6 dimethyl-Try, or 2,6 dihalo-Tyr, where halo is independently selected from fluoro, chloro, bromo, or iodo;
(3) B is an L-amino acid residue, a D-amino acid residue, D-Ser(O-t-butylether), D-Cys(S-t-butylthioether), or D-Met(sulfoxide);
(4) C is Gly, Phe, or nil;
(5) D is D' where D' is Phe, N-R$^2$-Phe, p-nitro-Phe, p-halo-Phe, Gly, or nil, where R$^2$ is lower alkyl and halo is fluoro, chloro, bromo, or iodo; or when E, F, G, H, and R$^1$ are nil, D is D' or Phe(ol);
(6) E is E' where E' is an L-amino acid residue, a D-amino acid residue, D-Pen or nil; or when F, G, H, and R$^1$ are nil, E is E', Met(sulfoxide)(ol), or Gly(ol);
(7) F is F' where F' is nil, Thr, or Thr(O-t-butylether); or where both G and H are other than nil, F is F', Arg, or Lys;
(8) G is nil; or where both F and H are other than nil, G is Arg, N-methyl-Arg, Lys, or nil;
(9) H is nil; or where both F and G are other than nil, H is D-Leu, Arg, Lys, or nil; and
(10) R$^1$ is hydroxy, amino, —NHR$^3$, —N(R$^3$)(R$^4$), —O—R$^3$, 2-acetylhydrazine, 2-propanoylhydrazine, N-aryl-alkyl-amine, chloromethyl, or nil; wherein R$^3$ and R$^4$ are independently selected from methyl, ethyl, or phenylethyl;

and wherein each peptide bond may be replaced by an isosteric linkage group.

5. A method of treatment for osteoporosis, according to claim 4, wherein B is Gly, D-Ala, D-Arg, D-Met, D-Set, D-Pen, D-Ser(O-t-butylether), D-Cys(S-t-butylthioether), or D-Met(sulfoxide); D is Phe; E is Leu, Nle, Met, Pro, Tyr, D-Pen, Gly(ol), Met(sulfoxide)(ol) or nil; F is Thr, Thr(O-t-butylether), or nil; G is nil; and H is nil; and wherein each peptide bond may be replaced by an isosteric linkage group.

6. A method of treatment for osteoporosis, according to claim 4, wherein said enkephalin consists of a polypeptide selected from the group consisting of H-Tyr-D-Cys(S-t-butylether)-Gly-Phe-Leu-Thr(O-t-butylether)-OH; H-Tyr-D-Ser(O-t-butylether)-Gly-Phe-Leu-Thr-OH; H-Tyr-D-Ser(O-t-butylether)-Gly-Phe-Leu-Thr(O-t-butylether)-OH; H-Tyr-D-Ala-Gly-N-methyl-Phe-Met(sulfoxide)(ol); H-Tyr-D-Ser-Gly-Phe-Leu-Thr-OH; H-Tyr-D-Ala-Gly-Phe-D-Leu-OH; H-Tyr-D-Ala-Gly-Phe-Leu-NH$_2$; H-Tyr-D-Ala-Gly-Phe-Met-NH$_2$; H-Tyr-D-Ala-Phe-Met-NH$_2$; H-Tyr-D-Met(sulfoxide)-Gly-Phe(ol); H-Tyr-D-Met-Gly-Phe-Pro-NH$_2$; H-2,6-dimethyl-Try-D-Ala-N-phenylpropylamine; and H-Tyr-D-Pen-Gly-Phe-D-Pen; H-Tyr-D-Ala-Gly-N-methyl-Phe-Gly(ol); wherein each peptide bond may be replaced by an isosteric linkage group.

7. A method of treatment for osteoporosis, according to claim 4, wherein said enkephalin is administered at a level of from about 0.05 mg/kg to about 5.0 mg/kg per day of said treatment.

8. A method of treatment for osteoporosis, according to claim 2, wherein said opioid is (SEQ ID NO: 1).

9. A method of treatment for osteoporosis, according to claim 1, wherein said active is an opioid-degrading enzyme inhibitor.

10. A method of treatment for osteoporosis, according to claim 9, wherein said opioid-degrading enzyme inhibitor is an enkephalin-degrading enzyme inhibitor.

11. A method of treatment for osteoporosis, according to claim 10, wherein said enkephalin-degrading enzyme inhibitor is selected from the group consisting of (DL-3-mercapto-2-benzylpropanoyl)-glycine; 1-(DL-3-mercapto-2-methylpropanoyl)-L-proline; 2-benzyl-3-(N-hydroxycarboxamido)-propanoyl-L-alanine; 2-benzyl-3-(N-hydroxy-carboxamido)-propanoyl-L-phenylalanine; (±)-N-(2-acetylthio)methyl-1-oxo-3-phenylpropyl glycine benzyl ester; N-morpholinyl-2-phenyl-methyl-3-mercaptopropanamide; alpha-(mercaptomethyl)-N-(4-pyridyl)-benzenepropanamide; N-[2-benzyl-3-(N-hydroxycarboxamido)-propanoyl]-3-amino-4-phenyl-butyric acid; N-[(R,S)-2-benzyl-3-[(S)(2-amino-4-methylthio)butyldithio]-1-oxopropyl]-L-Phe-benzyl ester; N-(2-benzyl-3-mercaptopropanoyl)

metanilic acid; and N-[(R,S)-2-carboxy-3-phenyl-propanoyl]-L-Leu.

12. A method of treatment for osteoporosis, according to claim 10, wherein said enkephalin-degrading enzyme inhibitor is administered at a level of from about 0.1 mg/kg to about 10.0 mg/kg per day of said treatment.

13. A method of treatment for osteoporosis, according to claim 1, wherein said active is an enkephalin secretagogue.

14. A method of treatment for osteoporosis, according to claim 13, wherein said enkephalin secretagogue is the peptide Tyr-Arg.

15. A method of treatment for osteoporosis, according to claim 13, wherein said enkephalin secretagogue is administered at a level of from about 0.05 mg/kg to about 10.0 mg/kg per day of said treatment.

16. A method of treatment for osteoporosis in a human or other animal subject, comprising: administering to said subject a safe and effective amount of an active selected from opioids, opioid-degrading enzyme inhibitors, enkephalin secretagogues, or a mixture thereof; and administering a non-active agent to said subject.

17. A method of treatment for osteoporosis, according to claim 16, wherein the non-active agent is selected from the group consisting of estrogen hormones, calcitonin, bisphosphonates, calcium, vitamin $D_3$, and mixtures thereof.

18. A method of treatment for osteoporosis, according to claim 17, wherein the non-active agent is conjugated estrogen.

19. A method of treatment for osteoporosis, according to claim 18, wherein the conjugated estrogen is administered to said subject at a level of from about 0.30 mg per day to about 1.25 mg per day of said treatment.

20. A method of treatment for osteoporosis, according to claim 19, wherein said conjugated estrogen is administered at a level of about 0.625 mg per day of said treatment.

21. A method of treatment for osteoporosis in a human or other animal subject, comprising administering to said subject a composition comprising
(a) a safe and effective amount of one or more actives selected from the group consisting of opioids, opioid-degrading enzyme inhibitors, enkephalin secretagogues, and mixtures thereof; and
(b) a pharmaceutically-acceptable carrier.

22. A method of treatment for osteoporosis in a human or others animal subject, comprising administering to said subject a safe and effective amount of an active selected from the group consisting of opioids, opioid-degrading enzyme inhibitors, enkephalin secretagogues, and mixtures thereof, wherein said active is administered in a cyclical regimen comprising a cycle that is repeated one or more times, said cycle comprising
(a) at least one active period of one or more days during which one or more of said actives are administered daily; and
(b) at least one non-active period of one or more days during which no active is administered.

23. A method of treatment for osteoporosis, according to claim 22, wherein said cycle comprises one active period followed by one non-active period.

24. A method of treatment for osteoporosis, according to claim 23, wherein an estrogen analog is administered daily during said active period and calcium is administered during said non-active period.

25. A method of treatment for osteoporosis, according to claim 24, wherein the active administered during the active period is an enkephalin-degrading enzyme inhibitor.

26. A method of treatment for osteoporosis, according to claim 25, wherein the active period is from about 10 days to about 40 days and the non-active period is from about 3 days to about 20 days.

27. A method of treatment for osteoporosis, according to claim 22, wherein said cycle comprises a first non-active period of one or more days, followed by an active period of one or more days, followed by a second non-active period of one or more days.

28. A method of treatment for osteoporosis, according to claim 27, wherein a bisphosphonate is administered daily during said first non-active period and calcium is administered daily during said second non-active period.

29. A method of treatment for osteoporosis, according to claim 28, wherein said first non-active period is from about 5 days to about 25 days in duration, said active period is from about 20 days to about 40 days in duration, and said second non-active period is from about 20 days to about 40 days in duration.

30. A method of treatment for osteoporosis, according to claim 29, wherein the active is an enkephalin-degrading enzyme inhibitor.

* * * * *

UNITED STATES PATENT AND TRADEMARK OFFICE
CERTIFICATE OF CORRECTION

PATENT NO. : 5,403,824
DATED : April 4, 1995
INVENTOR(S) : Sharyn M. D;Souza and Kenneth J. Ibbotson It is certified that error appears in the above-identified patent and that said Letters Patent is hereby corrected as shown below:

Col. 1, line 36, "Th is" should read --This--.

Col. 6, line 27, "$\leq$" should read --$\leq$--.

Col. 7, line 37, "$\leq$" should read --$\leq$--.

Col. 7, line 47, "[$^3$]" should read --[$^3$H]--.

Col. 7, line 58, "$\leq$" should read --$\leq$--.

Col. 8, line 30, "$\leq$" should read --$\leq$--.

Col. 8, line 50, "$\leq$" should read --$\leq$--.

Col. 12, line 57, "i s" should read --is--.

Col. 12, line 65, "Phe-AM(peptide" should read --Phe-AMC peptide--.

Col. 15, line 36, "where i n" should read --wherein--.

Col. 28, line 18, "$\leq$" should read --$\leq$--.

Col. 28, line 68, "$\leq$" should read --$\leq$--.

Col. 31, lines 29-33, the phrase "followed . . . of cycle." should go on the next line at the margin, not indented.

Signed and Sealed this

Twenty-seventh Day of February, 1996

BRUCE LEHMAN

*Attest:*

*Attesting Officer*     Commissioner of Patents and Trademarks